United States Patent [19]

Brown et al.

[11] Patent Number: 5,300,514

[45] Date of Patent: Apr. 5, 1994

[54] PYRAZOLIDINONE CCK AND GASTRIN ANTAGONISTS AND PHARMACEUTICAL FORMULATIONS THEREOF

[75] Inventors: Raymond F. Brown; J. Jeffry Howbert; Karen L. Lobb, all of Indianapolis; David A. Neel, Zionsville; Jon K. Reel, Carmel; Beverley Greenwood, Fishers, all of Ind.

[73] Assignee: Eli Lilly and Company, Indianapolis, Ind.

[21] Appl. No.: 33,737

[22] Filed: Mar. 18, 1993

Related U.S. Application Data

[63] Continuation of Ser. No. 982,257, Nov. 25, 1992, abandoned, which is a continuation of Ser. No. 737,624, Jul. 30, 1991, abandoned, which is a continuation-in-part of Ser. No. 553,489, Jul. 17, 1990, abandoned.

[51] Int. Cl.$^5$ .......................... A61K 31/415
[52] U.S. Cl. .................. 514/314; 514/338; 514/341; 514/404; 514/407; 546/146; 546/147; 546/174; 546/175; 548/162; 548/222; 548/369.7
[58] Field of Search ............... 514/314, 338, 341, 407; 546/146, 147, 174, 175; 548/364, 367, 374

[56] References Cited

U.S. PATENT DOCUMENTS

| | | | |
|---|---|---|---|
| 3,312,550 | 4/1967 | Stewart et al. ............... | 96/93 |
| 3,433,634 | 3/1969 | De Haes . | |
| 3,674,480 | 7/1972 | Kempfer et al. . | |
| 3,740,221 | 6/1973 | Willems et al. . | |
| 3,957,814 | 5/1976 | Moller et al. . | |
| 4,081,596 | 3/1978 | Moller et al. . | |
| 4,220,710 | 9/1980 | Janssens et al. ............ | 430/353 |
| 4,340,662 | 7/1982 | Ovshinsky et al. ......... | 430/270 |
| 4,902,708 | 2/1990 | Kim ............................. | 514/419 |

FOREIGN PATENT DOCUMENTS

| | | |
|---|---|---|
| 0155523 | 9/1985 | European Pat. Off. . |
| 0166355 | 1/1986 | European Pat. Off. . |
| 0373512 | 6/1990 | European Pat. Off. . |
| 2529786 | 1/1984 | France . |
| 767705 | 2/1957 | United Kingdom . |
| 1260939 | 1/1972 | United Kingdom . |

OTHER PUBLICATIONS

Neitzel et al., *Liebigs Ann. Chem.*, 1907–1912 (1980).
Howbert et al., Multiple Cholecystokinin Receptors—Progress Toward CNS Therapeutic Targets Abstract, Hawlow, England, Sep. 20–22, 1990.
Hodgkiss, et al. Multiple Cholecystokinin Receptors—Progress Toward CNS Therapeutic Targets Abstract, Harlow England, Sep. 20–22, 1990.
Lucaites et al., *Soc. Neurosci. Abstr.* 16:82, 1990.
Howbert et al., *Soc. Neurosci. Abstr.* 16:82, 1990.
Howbert, Joint Great Lakes–Central Regional Meeting of American Chemical Society, Indianapolis, Ind., May 29–31, 1991.
Howbert, Invited Lectures, McGill University (Nov. 28, 1990), Univ. Sherbrook (Nov. 29, 1990), Indiana Univ. School of Med. (Dec. 4, 1990; Dec. 6, 1990), Johns Hopkins Univ. (Jan. 29, 1991) Howbert, Society for Drug Research, Londong, England, Mar. 21, 1991.

*Primary Examiner*—C. Warren Ivy
*Assistant Examiner*—Raymond Covington
*Attorney, Agent, or Firm*—MaCharri R. Vorndran-Jones; Leroy Whitaker

[57] ABSTRACT

Novel substituted pyrazolidinones have been found to exhibit significant binding to cholecystokinin (CCK) receptors and gastrin receptors in the brain and/or peripheral sites such as the pancreas, stomach, and ileum. The pyrazolidinones are CCK and gastrin receptor antagonists and find therapeutic application in the treatment of gastrointestinal disorders, central nervous system disorders and for appetite regulation in warm-blood vertebrates. Pharmaceutical formulations for such indications are described.

13 Claims, No Drawings

PYRAZOLIDINONE CCK AND GASTRIN ANTAGONISTS AND PHARMACEUTICAL FORMULATIONS THEREOF

CROSS REFERENCE

This application is a continuation of application Ser. No. 07/982,257 filed Nov. 25, 1992, abandoned which is a continuation of Ser. No. 07/737,624, filed Jul. 30, 1991 (now abandoned), which is a continuation-in-part of Ser. No. 07/553,489, filed Jul. 17, 1990 (now abandoned).

BACKGROUND AND SUMMARY OF THE INVENTION

This invention relates to biologically active pyrazolidinones. More particularly, this invention is directed to certain substituted pyrazolidinones which bind to receptors for cholecystokinin (CCK), e.g., those of the brain and pancreas, and to receptors for gastrin, e.g., those of the stomach. The compounds are CCK and gastrin antagonists and are useful in the treatment and prevention of CCK and gastrin-related disorders of the gastrointestinal, central nervous and appetite regulatory systems of warm-blooded vertebrates, especially humans.

BACKGROUND OF THE INVENTION

Cholecystokinin (CCK) is a neuropeptide found in both gastrointestinal tissue and the tissues of the central nervous system. CCK is believed to play an important role in appetite regulation. Among the effects of CCK are stimulation of colonic motility, stimulation of gall bladder contraction, stimulation of pancreatic enzyme secretion, and inhibition of gastric emptying. CCK reportedly coexists with dopamine in certain mid-brain neurons and thus may also play a role in the functioning of dopaminergic systems in the brain Gastrin is a neuropeptide found particularly in the gastrointestinal tract. It is one of the primary natural stimulators of gastric acid secretion. It also has growth stimulatory effects on a variety of gastro-intestinal tissues.

CCK and gastrin antagonists are useful in the treatment and prevention of CCK and gastrin-related disorders of the gastrointestinal and central nervous systems, as well as modulation of the appetite regulatory systems of warm-blooded vertebrates. The CCK/gastrin receptor family is thought to contain three receptor subtypes, for which the location of the prototype receptor is given in parentheses: CCK-A (pancreas), CCK-B (brain), and gastrin (stomach fundus).

Several classes of CCK receptor antagonists have been reported in the literature. One class comprises derivatives of cyclic nucleotides, for example, dibutyryl cyclic GMP. Another art recognized class of CCK antagonists comprise the C-terminal fragments and analogs of CCK. Another class of CCK receptor antagonists are amino acid derivatives including proglumide, a derivative of glutaramic acid, and the N-acyltryptophanes such as p-chlorobenzoyl-L-tryptophan. More recently certain substituted amino phenyl compounds were described as CCK antagonists in published European Patent Application 0166355. Because of the wide range of potential clinical applications of CCK binding compounds, intensive research efforts have been ongoing to define other compounds exhibiting CCK receptor binding properties.

SUMMARY OF THE INVENTION

This invention is directed to novel pyrazolidinone compounds of Formula I or II below which have been found to exhibit CCK and gastrin antagonist activity. These compounds are useful in the treatment and prevention of CCK-related disorders of the gastrointestinal and central nervous systems, as well as in modulating the appetite regulatory systems of warm-blooded vertebrates, especially humans. As gastrin antagonists, they are particularly useful in the treatment and prevention of gastrointestinal ulcers, and of neoplasms of gastrointestinal origin.

DETAILED DESCRIPTION OF THE INVENTION

This invention is directed to compounds of the formula

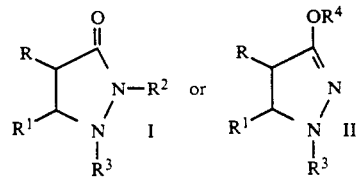

wherein $R$ and $R^1$ are independently hydrogen, $C_1$–$C_6$ alkyl, phenyl, benzyl, naphthyl, pyridyl or substituted phenyl having 1, 2, or 3 substituents selected from the group consisting of $C_1$–$C_6$ alkyl, $C_1$–$C_6$ alkoxy, $C_1$–$C_6$ alkylthio, halo, trifluoromethyl, phenyl, phenoxy, phenyl($C_1$–$C_4$ alkyl), phenyl($C_1$–$C_4$ alkoxy), phenylacetyl, $C_1$–$C_6$ alkanoyl, cyano, carbamyl, nitro, $C_1$–$C_6$ alkoxycarbonyl, methylenedioxy, $C_3$–$C_6$ alkylene, amino, —NH($C_1$–$C_4$ alkyl or benzyl) and N($C_1$–$C_4$ alkyl)$_2$;

$R_2$ is hydrogen, $C_1$–$C_6$ alkyl, carboxymethyl, $C_1$–$C_4$ alkoxycarbonylmethyl or a group of the formula

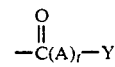

wherein t is 1 or 0; A is —CH$_2$—, —O—, —NH— or —N(-$C_1$–$C_6$ alkyl)—; and Y is phenyl or substituted phenyl as defined above;

$R_4$ is $C_1$–$C_6$ alkyl, carboxymethyl, or $C_1$–$C_4$ alkoxycarbonylmethyl;

$R_3$ is hydrogen or a group of the formula

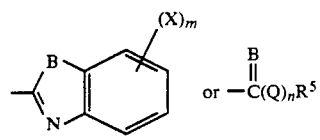

wherein B is O or S; X is selected from the phenyl substituents defined above; m is 0, 1 or 2; n is 0 or 1; Q is —NH—, —N($C_1$–$C_6$ alkyl)—, —S—, or —O—; and $R^5$ is a group of the formula —[CH($R^6$)]$_q$—(CH$_2$)$_r$—$R^7$ wherein $R^6$ is hydrogen or $C_1$–$C_6$ alkyl; q is 0 or 1; r is 0, 1 or 2; and $R^7$ is hydrogen, $C_1$–$C_8$ alkyl, $C_3$–$C_8$ cycloalkyl, pentafluorophenyl, pyridyl, tetrahydro-naphthyl, indolyl, quinolinyl, phenyl, naphthyl, or phenyl or naphthyl substituted with 1, 2, or 3 substituents as defined above for phenyl; or the group $-(Q)_nR^5$ is 2-tetrahydroisoquinolinyl; and the pharmaceutically acceptable salts thereof; provided that at least one of the groups R or $R^1$ is other than hydrogen or $C_1-C_6$ alkyl, and R or $R^1$ is hydrogen only when the other of R and $R^1$ is substituted phenyl in which the substituent is phenyl; and provided further that at least one of the groups $R_2$ and $R_3$ is other than hydrogen, and when $R^3$ is a group of the formula

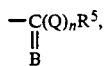

$R^2$ is other than a group of the formula

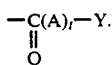

In the compounds of Formula I or II, the groups R and $R^1$ can be in either the cis or trans configuration relative to the plane of the pyrazolidinone ring. The trans configuration, preferred in accordance with the present invention, is indicated to be the thermodynamically favored form.

As used herein "halo" refers to fluoro, chloro, or bromo. The term "$C_1-C_6$ alkyl" includes both straight and branched chain alkyl and cycloalkyl and includes methyl, ethyl, propyl, cyclopropyl, isopropyl, butyl, methylcyclopropyl, cyclobutyl, isobutyl, t-butyl, pentyl, cyclopentyl, neopentyl, hexyl, cyclohexyl, 2-methylpentyl and the like. In the "$C_1-C_6$ alkoxy" and "$C_1-C_6$ alkylthio" substituents, the alkyl portion is $C_1-C_6$ alkyl as defined above. The term "$C_1-C_6$ alkanoyl" includes formyl, acetyl, propionyl, butyryl, pentanoyl, hexanoyl, and the like.

The term "pharmaceutically acceptable salts" encompasses those salts that form by standard acid-base reactions with basic groups (such as amino groups) and acidic groups, particularly carboxylic acid groups, on the compounds of Formula I or II. Thus, the pharmaceutically acceptable salts of the present invention can be prepared by conventional chemical methods from the compounds of Formula I or II which contain a basic or acidic moiety. Generally, the salts are prepared by reacting the free base or acid with a stoichiometric amount or with an excess of the desired salt-forming acid or base in a suitable solvent or combination of solvents. Suitable salt-forming acids include inorganic acids such as hydrochloric, hydrobromic, sulfuric, sulfamic, phosphoric, nitric, and the like; organic acids such as acetic, propionic, succinic, glycolic, stearic, lactic, citric, malic, tartaric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethanedisulfonic, oxalic, benzenesulfonic, picric, cinnamic, and like acids. Bases which find use for preparation of salts of compounds of Formula I or II having an acidic moiety include alkali or alkaline earth metal hydroxides such as sodium, potassium, lithium, calcium, or magnesium hydroxides, ammonia, or organic bases such as benzylamine, dibenzylamine, dibenzylethylenediamine, triethylamine, trimethylamine, piperidine, pyrrolidine, 2-hydroxyethylamine, bis(2-hydroxyethyl)amine, phenylethylbenzylamine, and like organic amines.

The compounds of this invention bind to CCK and gastrin receptors in the brain and/or peripheral sites such as the pancreas, gall bladder, stomach, and ileum. Their ability to antagonize CCK and gastrin makes these compounds useful as pharmaceutical agents for the treatment and prevention of disease states wherein CCK or gastrin may be involved, for example, gastrointestinal disorders such as irritable bowel syndrome, ulcers, excess pancreatic or gastric secretion, acute pancreatitis, motility disorders, neoplasms of gastrointestinal origin, central nervous system disorders involving CCK's interaction with dopamine, such as neuroleptic disorders, tardive dyskinesia, Parkinson's disease, psychosis or Gilles de la Tourette Syndrome, other CNS disorders where CCK is believed to be a causative factor, such as panic attacks and other forms of anxiety, and in modulating appetite regulatory systems.

Preferred CCK and gastrin receptor binding compounds of this invention are the pyrazolidinones of Formula I, particularly those wherein R and $R^1$ are in the trans configuration relative to the plane of the pyrazolidinone ring. Preferably, R and $R^1$ are phenyl or substituted phenyl. A preferred group of compounds of Formula I are those wherein $R^2$ is hydrogen and $R^3$ is a group of the formula

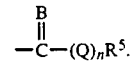

One series of such preferred compounds of this invention are those wherein B is sulfur, n is 1, Q is $-NH-$, and $R^5$ is phenyl or substituted phenyl.

Another preferred group of compounds exhibiting a consistent pattern of significant binding to CCK and gastrin receptors are those compounds of Formula I wherein $R^2$ is hydrogen and $R^3$ is a moiety defined by the group $-CONH-[CH(R^6)]_q-(CH_2)_r-R^7$. Especially preferred of those compounds are those wherein q and r are 0 and $R^7$ is phenyl, substituted phenyl, 2-naphthyl or 3-quinolinyl and R and $R^1$ are phenyl, naphthyl, or substituted phenyl in the trans configuration relative to the plane of the pyrazolidinone ring. When $R^7$ is substituted phenyl, preferred substituents are halo, more particularly, chloro, bromo or iodo; trifluoromethyl; $C_1-C_4$ alkyl; $C_3-C_4$ alkylene; benzyloxy; and methylthio.

The compounds of this invention are readily prepared from the corresponding compounds of the formula

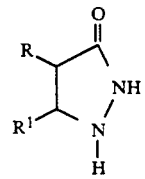

III

The intermediate 3-pyrazolidinones are readily prepared by reacting hydrazine with the corresponding $\alpha,\beta$-unsaturated esters of the formula $R^1-CH=C(-R)-COOR'$ wherein R and $R^1$ are as defined above and R' is an ester forming group, typically $C_1-C_6$ alkyl. The present compounds are prepared generally by acylating or alkylating the 3-pyrazolidinones of Formula III under neutral or basic conditions with acylating or alkylating agents selected to give the targeted compound of this invention.

In another embodiment of this invention there is provided pharmaceutical formulations comprising as an active ingredient an effective amount of a compound of Formula I or II and a pharmaceutically acceptable carrier, excipient or diluent therefor. Such formulations can be prepared for oral or parenteral administration for the treatment and prevention of disorders of the gastrointestinal, central nervous and appetite regulatory systems of warm-blooded vertebrates, especially a man.

For oral use of an antagonist of CCK or gastrin of this invention, the selected compound can be administered, for example, in the form of tablets or capsules, or as an aqueous solution or suspension. In the case of tablets, common excipients include binding agents, for example, syrup, acacia, gelatin, sorbitol, tragacanth, polyvinylpyrrolidine (Povidone), methylcellulose, ethylcellulose, sodium carboxymethylcellulose, hydroxypropylmethylcellulose, sucrose and starch; fillers and carriers, for example, corn starch, gelatin, lactose, sucrose, microcrystalline cellulose, kaolin, mannitol, dicalcium phosphate, sodium chloride and alginic acid; lubricants such as magnesium stearate; disintegrants such as croscarmellose, microcrystalline cellulose, corn starch, sodium starch glycolate and alginic acid; and suitable wetting agents such as lauryl sulfate. For oral administration in capsule form, useful diluents include lactose and dried corn starch. When aqueous suspensions are desirable for oral use, the active ingredient can be combined with emulsifying and suspending agents, for example, sorbitol, methylcellulose, glucose/sugar syrup, gelatin, hydroxyethylcellulose, carboxymethylcellulose, aluminum stearate gel or hydrogenated edible oils, for example, almond oil, fractionated coconut oil, oily esters, propylene glycol or ethyl alcohol; flavoring agents such as peppermint, oil of wintergreen, cherry flavoring or the like; and preservatives such as methyl or propyl p-hydroxybenzoates or ascorbic acid.

The pharmaceutical formulations in accordance with this invention can also be prepared for parenteral use. Such formulations typically take the form of sterile isotonic solutions of the active ingredient according to standard pharmaceutical practice.

The appropriate dose of the compound of the present invention for its use as an antagonist of CCK or gastrin in humans will vary according to the age, weight and response of the individual patient, as well as the severity of the patient symptoms and the nature of the condition being treated. Thus, the preferred daily dose will normally be determined by the prescribing physician. However, in most instances, effective daily doses of the compounds of this invention will range from about 0.05 mg to about 50 mg/kg and preferrably about 0.5 mg to about 20 mg/kg in a single or divided doses.

The following Examples are provided to describe further the compounds of this invention and methods for their preparation.

Tetrahydrofuran (THF) was dried by distillation from sodium/benzophenone. Reactions and workup steps were conducted at room temperature unless otherwise noted. Solvents were removed using a rotary evaporator at reduced pressure. Chromatography was performed on normal-phase silica columns except as noted. Titrations were performed in 2:1 DMF:H$_2$O as solvent.

EXAMPLE 1

1-[(4-Chloro-3-trifluoromethylphenyl)aminocarbonyl]-4,5-diphenyl-3-pyrazolidinone. [Method A]

4,5-Diphenyl-3-pyrazolidinone (3.00 g, 12.6 mmol) was dissolved in 40 mL THF under nitrogen, then a solution of 4-chloro-3-trifluoromethylphenylisocyanate (2.87 g, 13.0 mmol, 1.03 eq.) in 10 mL THF added over 2 min. After 2.3 hr, solvent was removed in vacuo, and the residue triturated with 25 mL toluene. The resulting solid was pulverized, washed twice with toluene, and dried in vacuo at 65° C. to give 4.94 g (85%) white solid.

$^1$H NMR (d$_6$-DMSO) δ 3.81 (br s, 1H), 5.56 (br s, 1H), 7.26–7.50 (m, 10H), 7.62 (d, J=9 Hz, 1H), 7.89 (dd, J=3, 9 Hz, 1H), 8.13 (br s, 1H), 9.64 (br s, 1H), 10.90 (br s, 1H); mass spectra (MS) 460 (M+1$^+$);

Analysis for C$_{23}$H$_{17}$ClF$_3$N$_3$O$_2$:
Calc.: C, 60.07; H, 3.73; N, 9.14;
Found: C, 59.99; H, 3.60; N, 8.89.

EXAMPLE 2

1-[(4-N,N-Dimethylaminophenyl)aminocarbonyl]-4,5-diphenyl-3-pyrazolidinone. [Method B]

4-N,N-Dimethylaminoaniline (2.00 g, 14.68 mmol) and triethylamine (3.63 g, 35.87 mmol, 2.44 eq.) were dissolved in 50 mL toluene under nitrogen, then triphosgene (1.45 g, 4.89 mmol, 0.333 eq.) added in one batch as a neat solid. The mixture was heated to reflux for 2.5 hr, cooled, then quickly filtered, the collected solid washed twice with toluene, and the combined filtrates evaporated in vacuo to give crude 4-N,N-dimethylaminophenylisocyanate as 2.57 g brown oil. This was redissolved in 50 mL THF and a solution of 4,5-diphenyl-3-pyrazolidinone (3.50 g, 14.69 mmol, 1.00 eq.) in 50 mL THF added over 3 min. After 20.7 hr, solvent was removed in vacuo and the product isolated by chromatography (preparative HPLC; 0–50% EtOAc:toluene gradient) as 1.73 g yellow oil which slowly crystallized. Recrystallization from toluene gave 744 mg (13%) white crystalline solid:

$^1$H NMR (d$_6$-DMSO) δ 2.84 (s, 6H), 3.71 (s, 1H), 5.55 (s, 1H), 6.67 (d, J=8 Hz, 2H), 7.12–7.52 (m, 12H), 8.86 (br s, 1H), 10.70 (br s, 1H); MS 400 (M+); titration pK$_a$'s 4.0, 7.9.

Analysis for C$_{24}$H$_{24}$N$_4$O$_2$:
Calc.: C, 71.98, H, 6.04, N, 13.99;
Found: C, 72.08, H, 6.06, N, 14.06.

EXAMPLE 3

1-[(4-Benzyloxyphenyl)aminocarbonyl]-4,5-diphenyl-3-pyrazolidinone [Method C]

4-Benzyloxybenzoic acid (2.0 g, 8.8 mmol) was suspended in 50 mL toluene with oxalyl chloride (5 mL) and heated to reflux for 15 min. Solvent was removed in vacuo, the residue redissolved in 30 mL acetone, and an aqueous solution of NaN$_3$ (1.16 g, 17.6 mmol, 2.0 eq. in 10 mL H$_2$O) added dropwise with external cooling by a water bath. The mixture was stirred for 1 hour, diluted with H$_2$O, extracted twice with toluene, then the combined extracts washed with water and brine, and dried over Na$_2$SO$_4$. This solution of acyl azide was treated with 4,5-diphenyl-3-pyrazolidinone (1.6 g, 6.8 mmol, 0.76 eq.), warmed until bubbles evolved, and heating maintained for 30 min. After stirring overnight at room temperature, the solvent was removed in vacuo, and the product isolated by chromatography (0–30% EtOAc:hexane gradient) as 1.6 g (52%) white solid: mp 127°–30° C.;

$^1$H NMR (CDCl$_3$) δ 3.95 (d, J=6 Hz, 1H), 5.0 (s, 2H), 5.55 (d, J=6 Hz, 1H), 6.8 (d, J=10 Hz, 2H), 6.86–7.46 (m, 16H), 7.05 (d, J=10 Hz, 2H), 8.95 (s, 1H); MS 463 (M+); titration pK$_a$ 7.7.

Analysis for C$_{29}$H$_{25}$N$_3$O$_3$:
Calc.: C, 75.14; H, 5.44; N, 9.07;
Found: C, 75.15; H, 5.49; N, 9.14.

EXAMPLE 4

1-[(2-[1,2,3,4-Tetrahydronaphthyl])aminocarbonyl]-4,5-diphenyl-3-pyrazolidinone [Method D]

1,2,3,4-Tetrahydro-2-naphthoic acid (639 mg, 3.63 mmol) was dissolved in 80 mL benzene under nitrogen, azeotropically dried by distilling a small portion of the solvent, then diphenylphosphorylazide (1.12 g, 4.08 mmol, 1.1 eq.) and Et$_3$N (0.41 g, 4.02 mmol, 1.1 eq.) added and the mixture heated to reflux for 1 hour. Solvent was removed in vacuo, the residue dissolved in dry THF under nitrogen, and 4,5-diphenyl-3-pyrazolidinone (784 mg, 3.29 mmol, 0.91 eq.) added and the mixture stirred overnight. The solvent was removed in vacuo and the product isolated by chromatography (25–50% EtOAc:hexane gradient) as 0.92 g (68%) white foam. Recrystallization of a 120 mg sample from i-Pr$_2$O:i-PrOH gave 94 mg white solid, containing a 1:1 mixture of two diastereomers by NMR: mp 82°–95° C.;

$^1$H NMR (CDCl$_3$) δ 1.46–1.66 (m, 1H), 1.79–1.97 (m, 1H), 2.30–2.84 (m, 2H), 2.95 (apparent t of d, J=6, 16 Hz, 1H), 3.87 (apparent d, J=6 Hz, 1H), 4.09 (m, 1H), 5.12 (m, 1H), 5.34 (apparent d of d, J=6, 14 Hz, 1H), 6.86–7.40 (m, 14 H), c. 9.0 (v br s, 1H); MS 411 (M+).

Analysis for C$_{26}$H$_{25}$N$_3$O$_2$:
Calc.: C, 75.89; H, 6.12; N, 10.21;
Found: C, 75.75; H, 6.32; N, 9.72.

EXAMPLE 5

1-[(3-Trifluoromethylbenzoyl]-4,5-diphenyl-3-pyrazolidinone [Method E]

A solution of 4,5-diphenyl-3-pyrazolidinone (2.0 g, 8.4 mmol) in 50 mL CH$_2$Cl$_2$ and 5 mL pyridine was treated dropwise with a solution of 3-trifluoromethylbenzoylchloride (1.4 g, 8.4 mmol) in 25 mL CH$_2$Cl$_2$ and stirred overnight. The mixture was washed with 1N HCl, dried over Na$_2$SO$_4$, evaporated, and the product isolated by chromatography (preparative HPLC) as 840 mg (24%) purple foam:

$^1$H NMR (CDCl$_3$) δ 3.83 (s, 1H), 5.16 (s, 1H), 7.2–7.64 (m, 15H); MS 410 (M+); titration pK$_a$ 7.15.

Analysis for C$_{23}$H$_{17}$F$_3$N$_2$O$_2$:
Calc.: C, 67.31; H, 4.18; N, 6.83;
Found: C, 67.52; H, 4.18; N, 6.66.

EXAMPLE 6

1-[(4-Chlorophenyl)oxycarbonyl]-4,5-diphenyl-3-pyrazolidinone [Method F]

A solution of 4,5-diphenyl-3-pyrazolidinone (1.25 g, 5.26 mmol) in 50 mL CHCl$_3$ was treated with a solution of 4-chlorophenylchloroformate (1.0 g, 5.26 mmol) in 10 mL CHCl$_3$ and stirred overnight. The solvent was removed in vacuo and the residue recrystallized from EtOAc:hexane to give 1.6 g (58%) white solid: mp 175°–7° C.

$^1$H NMR (CDCl$_3$) δ 3.98 (d, J=6 Hz, 1H), 5.62 (d, J=6 Hz, 1H), 6.8–7.5 (m, 15H); MS 392 (M+); titration pK$_a$ 7.8.

Analysis for C$_{22}$H$_{17}$ClN$_2$O$_3$:
Calc.: C, 67.26; H, 4.36; N, 7.13;
Found: C, 67.49, H, 4.54, N, 7.17.

EXAMPLE 7

1-[(3,4-Dichlorobenzyl)aminocarbonyl]-4,5-diphenyl-3-pyrazolidinone [Method M]

A solution of 1-[(4-nitrophenyl)oxycarbonyl]-4,5-diphenyl-3-pyrazolidinone (1.00 g, 2.48 mmol) and 3,4-dichlorobenzylamine (5 mL) in 50 mL abs. EtOH was heated to reflux for 8 hours. Solvent was removed in vacuo, the residue taken up in CH$_2$Cl$_2$, washed twice with 1N HCl and once with pH 7 buffer, and dried over Na$_2$SO$_4$. After removal of solvent in vacuo, the product was purified by chromatography (0–35% EtOAc:hexane gradient) to give 250 mg (23%) solid:

$^1$H NMR (CDCl$_3$) δ 3.93 (d, J=6 Hz, 1H), 4.28 (dABq, J=7, 15 (JAB) Hz, Δv=48 Hz, 2H), 5.50 (d, J=6 Hz, 1H), 5.56 (br t, J=7 Hz, 1H), 6.92–7.44 (m, 13H), 8.73 (br s, 1H); MS 439 (M+); titration pK$_a$ 8.4.

Analysis for C$_{23}$H$_{19}$Cl$_2$N$_3$O$_2$:
Calc.: C, 62.74; H, 4.35; N, 9.54;
Found: C, 62.49; H, 4.53; N, 9.25.

EXAMPLE 8

2-[(4-Chloro-3-trifluoromethylphenyl)aminocarbonyl]-4,5-diphenyl-3-pyrazolidinone [Method N]

1-[(4-Chloro-3-trifluoromethylphenyl)aminocarbonyl]-4,5-diphenyl-3-pyrazolidinone (2.00 g, 4.35 mmol) in 100 mL toluene was heated at reflux for 24 hours. After removal of solvent in vacuo, the rearranged product was isolated by chromatography (CH$_2$Cl$_2$), then recrystallized from i-Pr$_2$O:hexane, to give 300 mg (15%) white solid: mp 72°–4° C.

$^1$H NMR (CDCl$_3$) δ 4.22 (d, J=12 Hz, 1H), 4.82 (dd, J=9, 12 Hz, 1H), 5.44 (d, J=9 Hz, 1H), 7.20 (m, 2H), 7.32–7.42 (m, 8H), 7.46 (d, J=9 Hz, 1H), 7.72 (dd, J=3, 9 Hz, 1H), 7.87 (d, J=3 Hz, 1H), 10.56 (br s, 1H); MS 459 (M+).

Analysis for C$_{23}$H$_{17}$ClF$_3$N$_3$O$_2$:
Calc.: C, 60.07; H, 3.73; N, 9.14;
Found: C, 59.95; H, 3.92; N, 8.88.

EXAMPLE 9

1-[6-Chloro-2-benzothiazolyl]-4,5-diphenyl-3-pyrazolidinone [Method O]

The reaction was conducted under a dry nitrogen atmosphere. A suspension of 4,5-diphenyl-3-pyrazolidinone (1.19 g, 5.00 mmol) in 35 mL toluene was treated with 0.40 g NaH (60% in mineral oil; hydride content 0.24 g, 10.0 mmol, 2.00 eq.), and the mixture stirred at 45° C. for 2 hours. 2,6-Dichlorobenzothiazole (1.02 g, 5.00 mmol, 1.00 eq.) was added and stirring continued at 80° C. for 20 hours. After cooling, the reaction mixture was poured onto 30 mL ice-cooled 0.5N HCl, extracted with EtOAc, and the separated organic phase washed twice with brine, dried over Na$_2$SO$_4$, and the solvent evaporated in vacuo. The residue was recrystallized from Et$_2$O:hexane to provide 1.46 g (72%) light tan crystals: mp 170.5°–2.5° C.

$^1$H NMR (CDCl$_3$) δ 4.07 (br d, J=6 Hz, 1H), 5.24 (br d, J=6 Hz, 1H), 7.16–7.58 (m, 14H); MS 405 (M+); titration pK$_a$ 6.6.

Analysis for $C_{22}H_{16}ClN_3OS$:
Calc.: C, 65.10; H, 3.97; N, 10.35;
Found: C, 64.85; H, 4.13; N, 10.12.

EXAMPLE 10

1-[(4-Aminophenyl)aminocarbonyl]-4,5-diphenyl-3-pyrazolidinone

1-[(4-Nitrophenyl)aminocarbonyl]-4,5-diphenyl-3-pyrazolidinone (500 mg, 1.24 mmol) was dissolved in 50 mL EtOH and hydrogenated with 5% Pd/C (500 mg) under 60 p.s.i. $H_2$, overnight at room temperature. The mixture was filtered to remove catalyst, solvent removed in vacuo, and the product isolated by chromatography (0–50% EtOAc:hexane gradient) as 125 mg (27%) solid.

$^1$H NMR ($CDCl_3$) δ 3.97 (d, J=6 Hz, 1H), 5.50 (d, J=6 Hz, 1H), 6.58 (d, J=10 Hz, 2H), 6.96 (d, J=10 Hz, 2H), 7.2–7.5 (m, 10H); MS 372 (M+); titration p$K_a$ 4.5, 8.1.

Analysis for $C_{22}H_{20}N_4O_2$:
Calc.: C, 70.95; H, 5.41; N, 15.04;
Found: C, 70.65; H, 5.42; N, 14.75.

EXAMPLE 11

1-[(4-Bromophenyl)aminocarbonyl]-2-(O-t-butylcarboxymethyl)-4,5-diphenyl-3-pyrazolidinone and 1-[(4-bromophenyl)aminocarbonyl]-3(O-t-butylcarboxymethoxy)-4,5-diphenyl-2-pyrazoline To a suspension of 1-[(4-bromophenyl)aminocarbonyl]-4,5-diphenyl-3-pyrazolidinone (2.0 g, 4.6 mmol) in 30 mL abs. EtOH were added a solution of KOH (1.1 eq.) in abs. EtOH and t-butyl bromoacetate (5 mL). After stirring for 3 days a precipitate of KBr had appeared. The mixture was diluted with $H_2O$, extracted with $Et_2O$, then the $Et_2O$ layer washed with $H_2O$ and brine, dried over $Na_2SO_4$, and evaporated in vacuo. An inseparable mixture of two products was isolated by chromatography (0–25% EtOAc:hexane gradient) as 1.3 g (52%) foam, containing a 3:2 ratio of N-alkylated to O-alkylated products [first and second title products, respectively] by NMR:

$^1$H NMR ($CDCl_3$) N-alkylated: δ 1.53 (s, 9H), 3.96 (d, J=19 Hz, 1H), 4.06 (s, 1H), 4.65 (d, J=19 Hz, 1H), 5.95 (s, 1H), 7.23–7.46 (m, 14H), 9.70 (s, 1H); O-alkylated: δ 1.53 (s, 9H), 4.18 (d, J=7 Hz, 1H), 4.67 (s, 2H), 5.40 (d, J=7 Hz, 1H), 7.23–7.46 (m, 14H), 7.74 (s, 1H); MS 549, 551 (M+'s for Br isotopes).

Analysis for $C_{28}H_{28}BrN_3O_4$:
Calc.: C, 61.10; H, 5.13; N, 7.63;
Found: C, 60.94, H, 4.93; N, 7.85.

EXAMPLE 12

1-[(4-Bromophenyl)aminocarbonyl]-2-carboxymethyl-4,5-diphenyl-3-pyrazolidinone and 1-[(4-bromophenyl)aminocarbonyl]-3-carboxymethoxy-4,5-diphenyl-2-pyrazoline The regioisomeric mixture of t-butyl esters from Example 11 [c. 3:2 mixture of N- to O-alkylated] (500 mg, 0.91 mmol) was dissolved in 30 mL $CH_2Cl_2$ and 5 mL trifluoroacetic acid. After 4 hours TLC ($CH_2Cl_2$) indicated disappearance of starting materials. Solvent was removed in vacuo and a mixture of two products isolated by chromatography (0–100% EtOAc:hexane gradient) as 180 mg (40%) foam, comprised of a 4:3 ratio of N-alkylated to O-alkylated compounds [first and second title products, respectively] by NMR.

$^1$H NMR ($CDCl_3$) N-alkylated: δ 4.09 (d, J=2 Hz, 1H), 4.10 (d, J=19 Hz, 1H), 4.68 (d, J=19 Hz, 1H), 5.83 (d, J=2 Hz, 1H), 7.20–7.50 (m, 14H), 9.08 (s, 1H); O-alkylated: δ 4.19 (d, J=5 Hz, 1H), 4.83 (ABq, J=16 Hz, Δυ=30 Hz, 2H), 5.46 (d, J=5 Hz, 1H), 7.20–7.50 (m, 14H), 7.75 (s, 1H); MS 493, 495 (M+s for Br isotopes); titration p$K_a$ 4.8.

Analysis for $C_{24}H_{20}BrN_3O_4$:
Calc.: C, 58.31; H, 4.08; N, 8.50;
Found: C, 58.59; H, 4.03; N, 8.24.

The N- and O-alkylated products were separated by chromatography on a Waters $C_{18}$ reverse-phase column, using 30–40% $CH_3CN:H_2O$ buffered with 0.3–0.5% $NH_4OAc$. The leading fractions from the first pass were evaporated, lyophilized, then taken up in $CH_2Cl_2$, washed twice with 1N HCl, and the solvent removed in vacuo to provide 28 mg O-alkylated product:

$^1$H NMR ($CDCl_3$ δ 4.19 (d, J=7 Hz, 1H), 4.84 (ABq, J=17 Hz, Δυ=25 Hz, 2H), 5.45 (d, J=7 Hz, 1H), 6.39 (br s, 1H), 7.20–7.40 (m, 14H), 7.70 (s, 1H).

The later fractions were rechromatographed twice more, then similarly processed to give 8 mg N-alkylated product:

$^1$H NMR ($CDCl_3$) δ $CDCl_3$ 4.05 (s, 1H), 4.08 (br d, J=18 Hz, 1H), 4.70 (br d, J=18 Hz, 1H), 5.82 (s, 1H), 7.21–7.50 (m, 14H), 9.0 (br s, 1H).

EXAMPLE 13

1-[(4-Trifluoromethylphenyl)aminocarbonyl]-3-methoxy-4,5-diphenyl-2-pyrazoline

A solution of 1-[(4-trifluoromethylphenyl)aminocarbonyl]-4,5-diphenyl-3-pyrazolidinone (740 mg, 1.74 mmol) and KOH (122 mg of 88% pure, 1.1 eq.) in 30 mL abs. EtOH was treated with iodomethane (5 mL) and stirred overnight. The mixture was diluted with $H_2O$, extracted twice with $CH_2Cl_2$, and the combined extracts washed with $H_2O$, dried over $Na_2SO_4$, and evaporated in vacuo. The product was isolated by chromatography (0–15% EtOAc:hexane gradient) as 61 mg (8%) solid.

$^1$H NMR ($CDCl_3$) δ 4.0 (s, 3H), 4.11 (d, J=6 Hz, 1H), 5.48 (d, J=6 Hz, 1H), 7.2–7.74 (m, 14H), 8.09 (s, 1H); MS 439 (M+).

Also isolated was 1-[(4-trifluoromethylphenyl)aminocarbonyl]-2-methyl-4,5-diphenyl-3-pyrazolidinone, corresponding to a product prepared, according to the method of Example 1, from 2-methyl-4,5-diphenyl-3-pyrazolidinone and 4-trifluoromethylphenylisocyanate.

EXAMPLE 14

1-(Indole-2-carbonyl)-4,5-diphenyl-3-pyrazolidinone

Indole-2-carboxylic acid (1.35 g, 8.38 mmol), oxalyl chloride (4 mL), and DMF (3 drops) were added in order to 50 mL toluene, and stirred until gas evolution subsided and a homogeneous solution was obtained (c.20 min). Solvent was removed in vacuo, the residue taken up in $CH_2Cl_2$, and added to a solution of 4,5-diphenyl-3-pyrazolidinone (2.0 g, 8.40 mmol, 1.00 eq.) in 50 mL $CH_2Cl_2$ and 5 mL pyridine. After stirring overnight, the solution was washed with 1N HCl, dried over $Na_2SO_4$, and solvent removed in vacuo. The residual solid was stirred with $CH_2Cl_2$, filtered, and recrystallized from DMF:$H_2O$ to give 1.42 g (44%) white solid: mp 248°–50° C.

$^1$H NMR (d$_6$-DMSO) δ 3.82 (s, 1H), 5.86 (s, 1H), 6.95–7.6 (m, 16H), 11.84 (br s, 1H); MS 381 (M+); titration pK$_a$ 6.75.

Analysis for C$_{24}$H$_{19}$N$_3$O$_2$:

Calc.: C, 75.57; H, 5.02; N, 11.02;
Found: C, 75.38; H, 5.21; N, 10.99.

Examples 15–135 are summarized below in Table I. The compound of each Example is identified by reference to the structural formula preceeding each group of Examples The method for preparing each compound is indicated by reference to the Methods A-O, corresponding to the procedures identified in the foregoing Examples 1–9. Example 133A, and Examples 137–138 in Table II follow the same format. Examples 136, 139A/139B, 140–143 are illustrated separately to show physical chemistry data as well as the individual methods of preparation of these compounds. The phenyl groups on the pyrazolidinone ring of the compounds of Examples 1–67, 74–109, and 136–143 are in the trans position.

TABLE I
PHYSICAL CHEMISTRY DATA ON CCK/GASTRIN ANTAGONISTS

Structure for examples 15-59 below:

[Chemical structure showing a phenyl-substituted hydantoin/imidazolidinone with two phenyl groups and an N-aryl carbamate/urea bearing substituent R on the para position]

| Ex. | R | Method of Prep. | Solvent of Cryst.[a] | Yield, % | Mp. °C. | MS | 1HNMR | Formula | Analysis, % Theory/Found C | H | N |
|---|---|---|---|---|---|---|---|---|---|---|---|
| 15 | H | A | EtOAc:hexane | 22.0 g 73% | 168-70 | 357 (M+) | DMSO 3.75(s, 1H), 5.58(s, 1H), 6.96-7.53(m, 15H), 9.16(s, 1H), 10.8(s, 1H) | C22H19N3O2 | 73.93 73.84 | 5.36 5.42 | 11.76 11.75 |
| 16 | 4-CF3 | A (THF) | PhMe | 2.32 g 43.3% | | 426 (M + 1) | DMSO 3.80(br s, 1H), 5.58(br s, 1H), 7.30-7.80(m, 14H), 9.54(br s, 1H), 10.90(br s, 1H) | C23H18F3N3O2 | 64.94 64.67 | 4.26 4.09 | 9.88 9.75 |
| 17 | 4-F | A | EtOAc:hexane | 1.76 g 65% | 189-91 | 375 (M+) | CDCl3 3.99(d, J=6Hz, 1H), 5.53 (d, J=6Hz, 1H), 6.85-7.5(m, 14H), 8.95(br s, 1H) | C22H18FN3O2 | 70.37 70.24 | 4.83 4.85 | 11.17 11.09 |
| 18 | 4-Cl | A | EtOAc:hexane | 2.44 g 48% | 173-5 | 391 (M+) | DMSO 3.78(s, 1H), 5.56(s, 1H), 7.24-7.6((m, 14H), 9.32(s, 1H), 10.81(s, 1H) | C22H18ClN3O2 | 67.43 67.30 | 4.63 4.79 | 10.72 10.67 |
| 19 | 4-Cl (N—Me) | B | chrom (prep plates) | 60 mg 40% | | 405 (M+) | CDCl3 3.18(s, 3H), 3.53(d, J=3Hz, 1H), 4.86(d, J=3Hz, 1H), 6.9-7.42(m, 15H) | C23H20ClN3O2 | | | |
| 20 | 4-Br | A (THF) | PhMe (to give PhMe hemisolvate) | 2.64 g 58% | 174-6[b] | 435, 437 (M+'s for Br isotopes) | DMSO 3.77(br s, 1H), 5.57(br s, 1H), 7.12-7.55(m, 14H), 9.31(br s, 1H), 10.81(br s, 1H) | C22H18BrN3O2.¼(C7H8) | 63.49 63.15 | 4.60 4.60 | 8.71 8.81 |
| 21 | 4-I | C | EtOAc:hexane | 90 mg 2% | 177-9 | 483 (M+) | CDCl3 4.00(d, J=6Hz, 1H), 5.54(d, J=6Hz, 1H), 6.9-7.5(m, 14H) | C22H18IN3O2 | 54.67 54.46 | 3.75 3.70 | 8.69 8.51 |
| 22 | 4-CO2Et | A | chrom | 480 mg 11% | | 430 (M + 1) | CDCl3 1.38(t, J=8Hz, 3H), 4.02 (d, J=6Hz, 1H), 4.34(q, J=8Hz, 2H), 5.56(d, J=6Hz, 1H), 7.18-7.95(m, 14H) | C25H23N3O4 | | | |
| 23 | 4-COMe | A | chrom | 31 mg 1.2% | | 399 (M+) | CDCl3 2.52(s, 3H), 4.03(d, J=6Hz, 1H), 5.55(d, J=6Hz, 1H), 7.31 (d, J=12Hz, 2H), 7.2-7.5(m, 11Hz), 7.83(d, J=12Hz, 2H), 9.18(br s, 1H) | C24H21N3O3 | | | |
| 24 | 4-NO2 | A | EtOAc:hexane | 1.8 g 71% | 168-70 | 402 (M+) | DMSO 3.83(s, 1H), 5.58(s, 1H), 7.25-7.5m, 10H), 7.82(d, J=14Hz, 2H), 8.2(d, J=14Hz, 2H), 9.77 (s, 1H), 11.03(br s, 1H) | C22H18N4O4 | 65.67 65.43 | 4.51 4.56 | 13.92 13.70 |

TABLE I-continued
PHYSICAL CHEMISTRY DATA ON CCK/GASTRIN ANTAGONISTS

| | | | | | | | | | |
|---|---|---|---|---|---|---|---|---|---|
| 25 | 4-Me | A | PhMe | 1.72 g 44% | | 371 (M+) | DMSO 2.25(s, 3H), 3.75(s, 1H), 5.57(br s, 1H), 7.08(d, J=8Hz, 2H), 7.3–7.5(m, 12H), 9.03(br s, 1H), 10.74(br s, 1H) | C23H21N3O2 | 74.37 5.70 11.31 / 74.52 5.50 11.10 |
| 26 | 4-Et | A | triturated with PhMe | 3.74 g 92% | | 385 (M+) | DMSO 1.16(t, J=8Hz, 3H), 2.55 (q, J=8Hz, 2H), 3.74(br s, 1H), 5.57(br s, 1H), 7.12(d, J=9Hz, 2H), 7.14–7.54(m, 12H), 9.06(br s, 1H), 10.76(br s, 1H) | C24H23N3O2 | 74.78 6.01 10.90 / 75.00 6.13 10.71 |
| 27 | 4-n-Pr | C | EtOAc: hexane | 230 mg 6% | 169–71 | 400 (M+1) | CDCl3 0.9(t, J=10Hz, 3H), 1.58 (m, 2H), 2.5(t, J=10Hz, 2H), 4.0 (d, J=6Hz, 1H), 5.54(d, J=6Hz, 1H), 6.82(s, 1H), 7.03(d, J=12Hz, 2H), 7.1(d, J=12Hz, 2H), 7.23–7.5 (m, 10H), 8.62(br s, 1H) | C25H25N3O2 | 75.16 6.31 10.52 / 75.07 6.23 10.50 |
| 28 | 4-n-Bu | A | EtOAc: hexane | 1.22 g 47% | 165–7 | 413 (M+) | CDCl3 0.95(t, J=10Hz, 3H), 1.3 (m, 2H), 1.5(m, 2H), 2.56(t, J=10Hz, 2H), 3.96(d, J=6Hz, 1H), 5.54 (d, J=6Hz, 1H), 6.93(s, 1H), 7.03 (d, J=12Hz, 2H), 7.1(d, J=12Hz, 2H), 7.23–7.46(m, 10H), 9.04(s, 1H) | C26H27N3O2 | 75.52 6.58 10.16 / 75.23 6.35 9.97 |
| 29 | 4-I-Pr | A | THF: EtOAc | 10 g 40% | 191–3 | 399 (M+) | CDCl3 1.21(d, J=10Hz, 6H), 2.83 (m, 1H), 4.0(d, J=6Hz, 1H), 5.53(d, J=6Hz, 1H), 6.83(s, 1H), 7.1–7.5(m, 14H), 8.65(s, 1H) | C25H25N3O2 | 75.16 6.31 10.52 / 75.37 6.42 10.46 |
| 30 | 4-t-Bu | C | EtOAc | 790 mg 30% | 204–7 | 413 (M+) | CDCl3 1.26(s, 9H), 4.0(d, J=6Hz, 1H), 5.50(d, J=6Hz, 1H), 6.83(s, 1H), 7.12(d, J=12Hz, 2H), 7.35(d, J=12Hz, 2H), 7.2–7.44(m, 10H), 8.6(s, 1H) | C26H27N3O2 | 75.52 6.58 10.16 / 75.74 6.78 10.18 |
| 31 | 4-c-Hexyl | B | chrom, then EtOAc, then chrom | 104 mg 3% | 200–3 | 439 (M+) | DMSO 1.15–1.85(m, 10H), 2.22 (m, 1H), 3.74(s, 1H), 5.58(s, 1H), 7.13(d, J=12Hz, 1H), 7.46(d, J=12Hz, 1H), 7.3–7.43(m, 10H), 9.08(s, 1H), 10.76(s, 1H) | C28H29N3O2 | 76.51 6.65 9.56 / 76.29 6.81 9.38 |
| 32 | 4-Ph | C | chrom, then EtOAc: hexane | 312 mg 17% | 180–2 | 433 (M+) | CDCl3 4.02(d, J=6Hz, 1H), 5.60 (d, J=6Hz, 1H), 7.2–7.56(m, 20H), 9.4(br s, 1H) | C28H23N3O2 | 76.94 5.50 9.97 / 76.86 5.39 9.96 |
| 33 | 4-OMe | A | EtOAc: hexane | 1.9 g 79% | 154–7 | 387 (M+) | CDCl3 3.74(s, 3H), 3.96(d, J=6Hz, 1H), 5.53(d, J=6Hz, 1H), 6.74 (d, J=12Hz, 2H), 7.15(d, J=12Hz, 2H), 6.9–7.43(m, 11H), 9.0(br s, 1H) | C23H21N3O3 | 71.30 5.46 10.85 / 70.71 5.67 10.71 |
| 34 | 4-OEt | A | triturated with PhMe | 2.93 g 87% | | 401 (M+) | DMSO 1.31(t, J=7Hz, 3H), 3.73 (s, 1H), 3.97(q, J=7Hz, 2H), 5.55 (br s, 1H), 6.84(d, J=8Hz, 2H), 7.3–7.53(m, 12H), 8.99(br s, 1H), 10.72(br s, 1H) | C24H23N3O3 | 71.80 5.77 10.47 / 72.05 5.89 10.21 |
| 35 | 4-O—I-Pr | B | triturated with Et2O | 1.34 g 74% | 178–80 | 415 (M+) | CDCl3 1.27(d, J=5Hz, 1H), 3.93 (d, J=8Hz, 6H), 4.42(septet, J=6Hz, 1H), 5.54(d, J=5Hz, 1H), 6.72 (d, J=9Hz, 2H), 6.95(s, 1H), 7.05 | C25H25N3O3 | 72.27 6.06 10.11 / 72.25 6.04 10.06 |

TABLE I-continued
PHYSICAL CHEMISTRY DATA ON CCK/GASTRIN ANTAGONISTS

| # | R | | | mp | MS | NMR | Formula | Anal C | H | N |
|---|---|---|---|---|---|---|---|---|---|---|
| 36 | 4-OCH2CH2Ph | B | chrom (EtOAc: hexane), then triturated with PhMe | 324 mg 31% | 477 (M+) | (d, J=9Hz, 2H), 7.13-7.39(m, 11H) DMSO 3.01(t, J=7Hz, 2H), 3.73 (s, 1H), 4.14(t, J=7Hz, 2H), 5.55 (br s, 1H), 6.86(d, J=9Hz, 2H), 7.18-7.52(m, 17H), 9.01(br s, 1H), 10.72(br s, 1H) | C30H27N3O3 | 75.45 75.71 | 5.70 5.78 | 8.80 8.67 |
| 37 | 4-OPh | A | EtOAc: CH3OH | 2.9 g 68% | 188-90 | 450 (M+1) | DMSO 3.75(s, 1H), 5.59(s, 1H), 6.95-7.56(m, 19H), 9.21(s, 1H), 10.8(s, 1H) | C28H23N3O3 | 74.82 74.58 | 5.16 5.22 | 9.35 9.34 |
| 38 | 4-SMe | A | EtOAc: hexane | 1.6 g 65% | 160-2 | 403 (M+) | CDCl3 2.42(s, 3H), 4.0(d, J=6Hz, 1H), 5.54(d, J=6Hz, 1H), 6.95-7.44(m, 15H), 8.98(br s, 1H) | C23H21N3O2S | 68.46 68.28 | 5.25 5.28 | 10.41 10.25 |
| 39 | 3-CF3 | A | EtOAc: hexane | 3.0 g 83% | 165-7 | 425 (M+) | DMSO 3.8(s, 1H), 5.58(s, 1H), 7.3-7.56(m, 12H), 7.82(d, 1H), 7.98(s, 1H), 9.54(s, 1H), 10.88(s, 1H) | C23H18F3N3O2 | 64.94 65.07 | 4.27 4.19 | 9.88 9.77 |
| 40 | 3-NO2 | A | EtOAc: hexane | 2.11 g 84% | 164-6 | (no M+) | CDCl3 4.03(d, J=6Hz, 1H), 5.62 (d, J=6Hz, 1H), 7.2-8.1(m, 14H) | C22H18N4O4 | 65.57 65.53 | 4.51 4.25 | 13.92 13.67 |
| 41 | 3-Me | A | EtOAc: CH3OH | 1.05 g 46% | 188-90 | 371 (M+) | DMSO 3.3(s, 3H), 3.74(s, 1H), 5.57(s, 1H), 6.8-7.54(m, 12H), 9.04(s, 1H), 10.86(s, 1H) | C23H21N3O2 | 74.37 74.17 | 5.70 5.63 | 11.31 11.04 |
| 42 | 3-OMe | A | EtOAc: hexane | 2.1 g 51% | 163-5 | 387 (M+) | CDCl3 3.7(s, 3H), 3.98(d, J=6Hz, 1H), 5.54(d, J=6Hz, 1H), 6.56-7.48(m, 16H) | C23H21N3O3 | 71.30 71.29 | 5.46 5.72 | 10.85 10.59 |
| 43 | 3-O—i—Pr | B | C6H6: hexane | 450 mg 22% | 80-85 | 415 (M+) | CDCl3 1.26(d, J=6Hz, 6H), 3.96 (d, J=5Hz, 1H), 4.45(septet, J=6Hz, 1H), 5.51(d, J=5Hz, 1H), 6.54-6.62(m, 2H), 6.91-7.08(m, 3H), 7.21-7.50(m, 11H) | C25H25N3O3 | 72.27 71.99 | 6.06 6.18 | 10.11 9.94 |
| 44 | 3-OCH2Ph | B | triturated with Et2O | 1.64 g 85% | 143-44.5 | 463 (M+) | CDCl3 3.99(d, J=5Hz, 1H), 4.97 (s, 2H), 5.54(d, J=5Hz, 1H), 6.66-6.68(m, 2H), 7.06(s, 1H), 7.09-7.12(m, 2H), 7.23-7.44(m, 16H) | C29H25N3O3 | 75.14 75.01 | 5.44 5.49 | 9.07 8.84 |
| 45 | 3-CF3, 4-Br | B | chrom | 120 mg 12% | | 503, 505 (M+'s for Br isotopes) | CDCl3 4.03(d, J=6Hz, 1H), 5.58 d, J=6Hz, 1H), 7.2-7.56(m, 15H) | C23H17BrF3N3O2 | 54.78 55.05 | 3.40 3.51 | 8.33 8.07 |
| 46 | 3,4-diCl | A | EtOAc: hexane | 2.2 g 49% | 169-71 | 425 (M+) | CDCl3 4.04(d, J=6Hz, 1H), 5.57 (d, J=6Hz, 1H), 6.97-7.5(m, 15H) | C22H17Cl2N3O2 | 61.99 62.22 | 4.02 4.11 | 9.86 9.75 |
| 47 | 3-Cl,4-F | A | EtOAc: hexane | 2.0 g 84% | 174-6 | 409 (M+) | CDCl3 4.0(d, J=6Hz, 1H), 5.56(d, J=6Hz, 1H), 6.95-7.5(m, 15H) | C22H17ClFN3O2 | 64.47 64.03 | 4.18 4.76 | 10.25 9.53 |
| 48 | 3-NO2,4-Cl | A | EtOAc: hexane | 910 mg 41% | 149-51 | 536 (M+) | CDCl3 4.03(d, J=6Hz, 1H), 5.58 (d, J=6Hz, 1H), 7.2-7.82(m, 14H), 9.3(s, 1H) | C22H17ClN4O4 | 60.49 60.23 | 3.92 4.03 | 12.83 12.79 |
| 49 | 3,4-(CH2)3 | B | EtOAc: hexane, then chrom (EtOAc: hexane), then EtOAc | 380 mg 12% | 179-81 | 397 (M+) | DMSO 1.97(m, 2H), 2.8(m, 4H), 3.7(s, 1H), 5.58(s, 1H), 7.12-7.5 (m, 13H), 9.0(s, 1H), 10.75(s, 1H) | C25H23N3O2 | 75.55 75.67 | 5.83 5.95 | 10.57 10.46 |
| 50 | 3,4-(CH2)4 | D | chrom (EtOAc: CH2Cl2), then Et2O: CH2Cl2 | 354 mg 20% | 177-8.5 | 411 (M+) | CDCl3 1.74(t, J=3Hz, 4H), 2.66 (d, J=7Hz, 4H), 3.97(d, J=5Hz, 1H), 5.55(d, J=5Hz, 1H), 6.83-6.92(m, 3H), 6.98(s, 1H), 7.24-7.44(m, 10H), 9.06(br s, 1H) | C26H25N3O2 | 75.89 76.08 | 6.12 6.33 | 10.21 10.05 |

TABLE I-continued
PHYSICAL CHEMISTRY DATA ON CCK/GASTRIN ANTAGONISTS

| | | | | | | | | | |
|---|---|---|---|---|---|---|---|---|---|
| 51 | 3,4-DiOMe | chrom | 640 mg 11% | | 418 (M+) | CDCl3 3.74(s, 3H), 3.82(s, 3H), 3.97(d, J=6Hz, 1H), 5.58(d, J=6Hz, 1H), 6.53–7.5(m, 14H), 8.7(s, 1H) | C24H23N3O4 | 69.05 68.92 | 5.55 5.54 | 10.07 10.12 |
| 52 | 3,4-OCH2O | B | 390 mg 7% | 179–81 | 401 (M+) | DMSO 3.73(s, 1H), 5.55(s, 1H), 5.97(s, 2H), 6.8–7.6(m, 13H), 9.05(s, 1H), 10.75(s, 1H) | C23H19N3O4 | 68.82 68.96 | 4.77 4.76 | 10.47 10.29 |
| 53 | 2-CF3 | A | 3.46 g 77% | 143–5 | 425 (M+) | DMSO 3.8(s, 1H), 5.6(s, 1H), 7.2–7.75(m, 14H), 8.68(s, 1H), 10.95 (s, 1H) | C23H18F3N3O2 | 64.94 65.15 | 4.26 4.19 | 9.88 9.60 |
| 54 | 2,3-diCl | A | 3.9 g 70% | 191–3 | 425 (M+) | DMSO 3.78(s, 1H), 5.54(s, 1H), 7.3–7.6(m, 13H), 8.88(s, 1H), 11.05(s, 1H) | C22H17Cl2N3O2 | 61.93 62.00 | 4.02 3.96 | 9.86 9.94 |
| 55 | 2,4-diCl | A | 1.7 g 63% | 150–3 | 425 (M+) | CDCl3 4.02(d, J=6Hz, 1H), 5.38 (d, J=6Hz, 1H), 7.15–7.5(m, 13H), 8.1(d, J=10Hz, 1H), 8.95(s, 1H) | C22H17Cl2N3O2 | 61.98 62.16 | 4.02 4.28 | 9.86 9.96 |
| 56 | 2,4-diF | A | 800 mg 32% | | 393 (M+) | CDCl3 4.03(d, J=6Hz, 1H), 5.43 (d, J=6Hz, 1H), 6.8(m, 2H), 6.91 (s, 1H), 7.2–7.5(m, 9H), 7.93(m, 1H), 8.8(br s, 1H) | C22H17F2N3O2 | | | |
| 57 | 2-Cl,5-CF3 | A | 1.38 g 29% | 130–2 | 459 (M+) | CDCl3 4.05(d, J=6Hz, 1H), 5.41 (d, J=6Hz, 1H), 7.2–7.5(m, 14H), 8.53(s, 1H) | C23H17ClF3N3O2 | 60.07 60.37 | 3.73 3.95 | 9.14 9.03 |
| 58 | 3,5-diCF3 | A | 3.6 g 69% | | 493 (M+) | CDCl3 4.03(d, J=6Hz, 1H), 5.62 (d, J=6Hz, 1H), 7.2–7.58(m, 13H), 7.75(s, 2H) | C24H17F6N3O2 | 58.42 58.59 | 3.47 3.75 | 8.52 8.69 |
| 59 | 3,5-diCl | A | 800 mg 30% | 166–8 | 425 (M+) | DMSO 3.82(s, 1H), 5.54(s, 1H), 7.2(s, 1H), 7.15–7.5(m, 10H), 7.71 (s, 2H), 9.5(s, 1H), 10.95(s, 1H) | C22H17Cl2N3O2 | 61.99 61.75 | 4.02 3.94 | 9.86 9.65 |

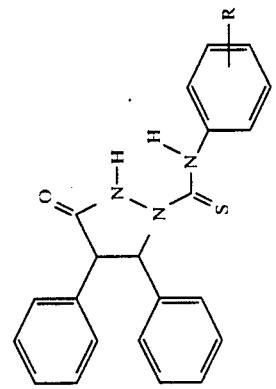

| | | | | | | | | | |
|---|---|---|---|---|---|---|---|---|---|
| 60 | H | A (THF) | PhMe: hexane then Et2O: hexane (to give Et2O solvate) | 117 mg 5% | 69–79 | 373 (M+) | CDCl3 4.03(d, 1H), 5.77(d, 1H), 7.10–7.54(m, 16H), 9.6(br s, 1H) [plus for Et2O: 1.20(t, 6H), 3.48 (q, 4H)] | C22H19N3OS.C4H10O | 69.77 69.72 | 6.53 6.38 | 9.39 9.37 |
| 61 | 3-CF3 | A | chrom | 1.5 g 33% | | 442 (M+) | CDCl3 4.07(d, J=6Hz, 1H), 5.82 (d, J=6Hz, 1H), 7.12–7.63(m, 16H) | C23H18F3N3OS | 62.58 62.87 | 4.11 4.22 | 9.52 9.34 |
| 62 | 4-CF3 | A | PhMe | 800 mg 29% | 87–90 | 441 (M+), 442 (M+1) | CDCl3 4.09(d, J=6Hz, 1H), 5.77 (d, J=6Hz, 1H), 7.16(d, J=9Hz, 1H), 7.2–7.28(m, 3H), 7.3–7.44 | C23H18F3N3OS | 62.51 62.51 | 4.11 4.15 | 9.52 9.46 |

TABLE I-continued
PHYSICAL CHEMISTRY DATA ON CCK/GASTRIN ANTAGONISTS

| Ex. | | Method of Prep. | Solvent of Cryst.[a] | Yield, % | Mp. °C. | MS | 1HNMR | Formula | Analysis, % Theory/Found C | H | N |
|---|---|---|---|---|---|---|---|---|---|---|---|
| 63 | 3-CF3,4-Cl | A | chrom, then triturated with hexane | 200 mg 10% | 80-2 | 475 (M+), 476 (M + 1) | (m, 7H), 7.44-7.64(m, 5H) CDCl3 4.09(d, J=6Hz, 1H), 5.83 (d, J=6Hz, 1H), 7.06-7.6(m, 15H) | C23H17ClF3N3OS | 58.05 58.15 | 3.60 3.62 | 8.83 8.55 |
| 64 | 2,3-diCl | A | EtOAc: hexane | 2.5 g 67% | 154-6 | 441 (M+), 442, 444 (M + 1's for Cl isotopes) | DMSO 3.95(s, 1H), 6.16(s, 1H), 7.2-7.6(m, 13H), 9.5(br s, 1H), 11.5(br s, 1H) | C22H17Cl2N3OS | 59.73 59.92 | 3.87 4.11 | 9.50 9.73 |
| 65 | pentaF | A | chrom | 600 mg 21% | | 463 (M+) | CDCl3 4.04(d, J=5Hz, 1H), 5.82 (s, 1H), 6.94(s, 1H), 7.2-7.55(m, 1H) | C22H14F5N3OS | | | |

| Ex. | R | R' | Method of Prep. | Solvent of Cryst.[a] | Yield, % | Mp. °C. | MS | 1HNMR | Formula | Analysis, % Theory/Found C | H | N |
|---|---|---|---|---|---|---|---|---|---|---|---|---|
| 66 | 2,3-diCl | Me | A | EtOAc: hexane chrom | 670 mg 76% | 172-4 | 439 (M+) | DMSO 3.35(s, 3H), 3.88(s, 1H), 5.50(s, 1H), 7.16-7.56(m, 13H), 9.26(s, 1H) | C23H19Cl2N3O2 | 62.74 62.55 | 4.35 4.26 | 9.54 9.37 |
| 67 | 4-CF3 | Me | A | | 210 mg 40% | | 439 (M+) | CDCl3 3.36(s, 3H), 3.93(d, J=3Hz, 1H), 5.54(d, J=3Hz, 1H), 6.92(s, 1H), 7.15-7.6(m, 14H) | C24H20F3N3O2 | 65.60 65.35 | 4.59 4.51 | 9.56 9.30 |
| 68 | 2,3-diCl | Ph | A | EtOAc | 170 mg 63% | 172-3 | 425 (M+) | DMSO 2.5(m, 1H), 3.53(m, 1H), 5.72(s, 1H), 7.3-7.76(m, 11H), 7.95(s, 1H), 8.58 (s, 1H), 10.6(br s, 1H) | C22H17Cl2N3O2 | 61.96 62.20 | 4.02 4.04 | 9.86 9.94 |

TABLE I-continued
PHYSICAL CHEMISTRY DATA ON CCK/GASTRIN ANTAGONISTS

| | | Method | Solvent | Yield, Mp. | | | | Analysis, % Theory/Found | | |
|---|---|---|---|---|---|---|---|---|---|---|
| 69 | 4-Br | n-Bu | A | chrom | 670 mg 56% | | 415, 417 (M+'s for Br isotopes) | DMSO 0.84(t, J=12Hz, 3H), 1.30(m, 2H), 1.46(m, 2H), 1.65(m, 2H), 3.29(s, 1H), 5.38(s, 1H), 7.2–7.6(m, 9H), 9.17 (s, 1H), 10.34(s, 1H) | C20H22BrN3O2 | | |
| 70 | 3-CF3 | n-Bu | A | chrom | 290 mg 21% | | 405 (M+) | CDCl3 0.93(t, J=12Hz, 3H), 1.42(m, 2H), 1.5(m, 2H), 1.73(m, 1H), 1.83(m, 1H), 3.79(s, 1H), 4.83(m, 1H), 7.2–7.6 (m, 9H), 7.74(s, 1H), 7.83(s, 1H) | C21H22F3N3O2 | 62.21 62.40 | 5.47 5.66 | 10.36 10.26 |
| 71 | 4-CF3 | n-Bu | A | chrom | 136 mg 15% | 152–5 | 405 (M+) | CDCl3 0.95(t, J=8Hz, 3H), 1.42(m, 2H), 1.51(m, 2H), 1.72(m, 1H), 1.88 (m, 1H), 3.53(s, 1H), 4.82(t, J=8Hz, 1H), 7.18–7.35(m, 5H), 7.44(ABq, J=8Hz, Δν=18Hz, 4H), 7.65(s, 1H), 8.55 (vbr s, 1H) | C21H22F3N3O2 | 62.21 61.97 | 5.47 5.56 | 10.36 10.22 |
| 72 | 4-Br | CH2Ph | A | EtOAc: hexane | 248 mg 51% | | 449, 451 (M+'s for Br isotopes) | DMSO 2.97–3.15(m, 2H), 3.47(br s, 1H), 4.70(br s, 1H), 7.01(d, J=8Hz, 2H), 7.15–7.42(m, 12H), 9.05(br s, 1H), 10.47(br s, 1H) | C23H20BrN3O2 | 61.34 61.16 | 4.48 4.73 | 9.33 9.12 |
| 73 | 4-Br | i-Pr | A | chrom (EtOAc: hexane) | 45 mg 42% | | 401, 403, (M+'s for Br isotopes) | CDCl3 1.12(d, J=6Hz, 6H), 2.05(m, J=7Hz, 1H), 3.64(s, 1H), 4.56(d, J=8Hz, 1H), 7.20–7.51(m, 9H), 8.28(br s, 1H) | C19H20BrN3O2 | | | |

TABLE I-continued
PHYSICAL CHEMISTRY DATA ON CCK/GASTRIN ANTAGONISTS

Structure for Ex. 74-81:

[Structure: pyrrolidinone with N-C(=O)-X-phenyl-R substituent and two phenyl groups on adjacent carbons]

| Ex. | R | X | of Prep. | of Cryst.[a] | % | °C. | MS | 1HNMR | Formula | C | H | N |
|---|---|---|---|---|---|---|---|---|---|---|---|---|
| 74 | 4-CF3 | — | E (Et3N) | c | 100 mg 6% | 72-5 | 410 (M+) | CDCl3 3.89(d, J=4Hz, 1H), 5.16(br s, 1H), 7.18-7.26(m, 5H), 7.26-7.50(m, 8H), 7.50-7.57(m, 2H) | C23H17F3N2O2 | 67.31 67.57 | 4.18 4.45 | 6.83 6.64 |
| 75 | 3,4-diCl | — | E (no base) | c | 508 mg 29% | 68-70 | 410, 412 (M+'s for Cl isotopes) | CDCl3 3.89(d, J=4Hz, 1H), 5.18(br s, 1H), 7.14-7.48(m, 14H) | C22H16Cl2N2O2 | 64.25 64.21 | 3.92 3.99 | 6.81 6.60 |
| 76 | 3-CF3 | CH2 | E | chrom | 600 mg 17% | | 424 (M+) | CDCl3 3.47(s, 2H), 3.94(s, 1H), 5.30 (s, 1H), 7.0-7.8(m, 14H) | C24H19F3N2O2 | 67.92 67.76 | 4.51 4.56 | 6.60 6.79 |
| 77 | 4-CF3 | CH2 | E (no base) | c | 101 mg 6% | 66-68 | 424 (M+) | CDCl3 3.48(br s, 2H), 3.91(d, J=4Hz, 1H), 5.28(br s, 1H), 7.04-7.5(m, 15H) | C24H19F3N2O2 | 67.92 67.78 | 4.51 4.56 | 6.60 6.45 |
| 78 | 3,4-diCl | CH2 | E (Et3N) | Et2O: hexane | 1.0 g 17% | 70-72 | 426 (M+) | CDCl3 3.36(br s, 2H), 3.93(d, J=5Hz, 1H), 5.27(br s, 1H), 6.84(br s, 1H), 7.0 (br s, 1H), 7.08-7.5(m, 12H) | C23H18Cl2N2O2 | 64.95 64.93 | 4.27 4.67 | 6.58 6.60 |
| 79 | H | O | F | EtOAc: hexane | 980 mg 43% | 164-6 | 358 (M+) | CDCl3 3.97(d, J=6Hz, 1H), 5.54(d, J=6Hz, 1H), 6.9-7.5(m, 16H) | C22H18N2O3 | 73.73 73.94 | 5.06 5.29 | 7.82 7.88 |
| 80 | 4-NO2 | O | F | EtOAc | 1.3 g 32% | 175-7 | 403 (M+) | CDCl3 4.02(d, J=6Hz, 1H), 5.52(d, J=6Hz, 1H), 7.1-7.5(m, 12H), 8.19(d, J=15Hz, 2H), 9.25(br s, 1H) | C22H17N3O5 | 65.51 65.49 | 4.25 4.31 | 10.42 10.34 |
| 81 | 4-Br | S | B | EtOAc: hexane | 610 mg 13% | 156-7 | 452, 454 (M+'s for Br isotopes) | CDCl3 3.97(d, J=4Hz, 1H), 5.58(d, J=4Hz, 1H), 7.25-7.55(m, 14H), 9.15 (br s, 1H) | C22H17BrN2O2S | 58.29 58.04 | 3.78 3.79 | 6.18 6.07 |

Structure for Ex. 82:

[Structure: pyrrolidinone with two phenyl groups and N-C(=O)-X-phenyl-R substituent with NH]

| Ex. | R | X | of Prep. | of Cryst.[a] | % | °C. | MS | 1HNMR | Formula | C | H | N |
|---|---|---|---|---|---|---|---|---|---|---|---|---|
| 82 | 3-CF3 | NH | N | chrom (CH2Cl2) | 1.72 g 48% | | 425 (M+) | CDCl3 4.22(d, J=12Hz, 1H), 4.82 (dd, J=9Hz, 12Hz, 1H), 5.46(d, J=9Hz, | C23H18F3N3O2 | | | |

TABLE I-continued
PHYSICAL CHEMISTRY DATA ON CCK/GASTRIN ANTAGONISTS

| Ex. | R | X | | Method of Prep. | Solvent of Cryst.a | Yield, % | Mp, °C. | MS | 1HNMR | Formula | Analysis, % Theory/Found C | H | N |
|---|---|---|---|---|---|---|---|---|---|---|---|---|---|
| 83 | 4-CF3 | NH | N | chrom (CH2Cl2), then triturated with hexane | | 530 mg 30% | 74-6 | 425 (M+) | 1H), 7.18-7.75(m, 13H), 7.84(s, 1H), 10.35(s, 1H) CDCl3 4.23(d, J=12Hz, 1H), 4.82 dd, J=9, 12Hz, 1H), 5.44(d, J=9Hz, 1H), 7.18-7.24(m, 2H), 7.3-7.42(m, 8H), 7.56-7.7(m, 4H), 10.4(br s, 1H) | C24H18F3N3O2 | 64.94 65.11 | 4.27 4.41 | 9.88 9.65 |

| 84 | H | S | | O (C6H6) | | 233 mg 42% | 186-8 | 371 (M+) | CDCl3 4.05(d, 1H), 5.23(d, 1H), 7.15-7.68(m, 15H) | C22H17N3Os | 71.14 71.38 | 4.61 4.89 | 11.31 11.11 |
| 85 | 6-Br | S | | O (PhMe) | | 1.67 g 57% | 180-6 | 449, 451 (M+'s for Br isotopes) | CDCl3 4.06(d, J=7Hz, 1H), 5.24(d, J=7Hz, 1H), 7.16-7.52(m, 13H), 7.64 (d, J=1Hz, 1H) | C22H16BrN3OS | 58.67 58.87 | 3.58 3.83 | 9.33 9.08 |
| 86 | 4,5-diCl | S | | O (PhMe) | | 1.10 g 83% | 200-4 | 440 (M+1 for Cl isotopes) | CDCl3 4.13(d, J=8Hz, 1H), 5.19(d, J=8Hz, 1H), 7.18-7.45(m, 13H) | C22H15Cl2N3OS | 60.01 60.30 | 3.43 3.70 | 9.54 9.62 |
| 87 | H | O | | O (PhMe) | | 660 mg 62% | 174-5.5 5.5 | 355 (M+) | CDCl3 4.04(d, J=4.5Hz, 1H), 5.60(d, J=4.5Hz, 1H), 7.14-7.54(m, 15H) | C22H17N3O2 | 74.35 74.56 | 4.82 4.98 | 11.82 11.67 |

Structure for examples 88-108 below

| Ex. | R | | | Method of Prep. | Solvent of Cryst.a | Yield, % | Mp, °C. | MS | 1HNMR | Formula | Analysis, % Theory/Found C | H | N |
|---|---|---|---|---|---|---|---|---|---|---|---|---|---|
| 88 | 3-Pyridyl | | | C | precipitated | 3.5 g | 208-10 | 358 (M+) | DMSO 3.8(s, 1H), 5.54(s, 1H), 7.27- | C21H18N4O2 | 70.38 | 5.06 | 15.63 |

TABLE I-continued
PHYSICAL CHEMISTRY DATA ON CCK/GASTRIN ANTAGONISTS

| # | R | Method | Purification | Yield | mp | MS | NMR | Formula | %C | %H | %N |
|---|---|---|---|---|---|---|---|---|---|---|---|
| 89 | 4-Pyridyl | C | from reaction mixture | 73% | | 358 (M+) | 7.5(m, 1H), 7.94(m, 1H), 8.23(m, 1H), 8.7(m, 1H), 9.38(br s, 1H), 10.94(br s, 1H) | C21H18N4O2 | 70.34 | 5.16 | 15.35 |
| 90 | 1-Naphthyl | A | chrom | 183 mg 28% | | 407 (M+) | CDCl3 3.93(d, J=6Hz, 1H), 5.46(d, J=6Hz, 1H), 7.18-7.35(m, 10H), 7.62 (d, J=10Hz, 2H), 7.95(d, J=10Hz, 2H) | C26H21N3O2 | 76.64 76.41 | 5.19 5.33 | 10.31 10.12 |
| 91 | 2-Naphthyl | A | EtOAc: hexane | 790 mg 33% | 145-7 | 407 (M+) | CDCl3 4.03(d, J=6Hz, 1H), 5.51(d, J=6Hz, 1H), 6.8-7.8(m, 18H), 9.0(br s, 1H) | C26H21N3O2 | 76.64 76.83 | 5.19 5.27 | 10.31 10.26 |
| 92 | 3-Quinolinyl | D | EtOAc: hexane | 1.13 g 44% | 172-4 | 409 (M+) | CDCl3 4.02(d, J=6Hz, 1H), 5.60(d, J=6Hz, 1H), 7.1-7.9(m, 18H), 9.38 (br s, 1H) | C25H20N4O2 | 73.51 73.48 | 4.93 4.74 | 13.71 13.55 |
| 93 | 6-Quinolinyl | D | THF: PhMe (came out of reaction mixture) | 157 mg 12% | 244-6.5 | 408 (M+) | DMSO 3.81(s, 1H), 5.57(s, 1H), 7.29-7.62(m, 12H), 7.85(d, J=8Hz, 1H), 7.91(d, J=8Hz, 1H), 8.44(d, J=2Hz, 1H), 8.97(d, J=2Hz, 1H), 9.62(br s, 1H), 11.00(br s, 1H) | C25H20N4O2 | 73.51 73.68 | 4.94 5.09 | 13.72 13.57 |
| 94 | n-Bu | A | CH3CN: PhMe | 224 mg 32% | 222-5 | 337 (M+) | DMSO 3.79(s, 1H), 5.58(s, 1H), 7.25-7.49(m, 11H), 7.85-7.93(m, 2H), 8.14(d, J=1.4Hz, 1H), 8.20(d, J=8Hz, 1H), 8.74(dd, J=1.4, 4.3Hz, 1H), 9.45(br s, 1H), 10.95(br s, 1H) | C20H23N3O2 | 71.19 71.33 | 6.87 6.71 | 12.45 12.27 |
| 95 | c-Hexyl | A | chrom | 2.68 g 76% | | 363 (M+) | DMSO 0.86(t, J=10Hz, 3H), 1.15(m, 2H), 1.38(m, 2H), 3.08(m, 2H), 3.62 (s, 1H), 5.47(s, 1H), 7.18(s, 1H), 7.3-7.46(m, 10H), 10.52(s, 1H) | C22H25N3O2 | 72.70 72.59 | 6.93 7.03 | 11.56 11.30 |
| 96 | CH2Ph | A | EtOAc: hexane | 1.9 g 83% | 152-4 | 371 (M+) | CDCl3 0.8-1.84(m, 10H), 3.6(m, 1H), 3.89(d, J=6Hz, 1H), 4.98(d, J=12Hz, 1H), 5.42(d, J=6Hz, 1H), 7.2-7.45(m, 10H), 8.66(s, 1H) | C23H21N3O2 | 74.37 74.11 | 5.70 5.77 | 11.31 11.12 |
| 97 | CH2Ph(N—Me) | A | chrom | 2.6 g 67% | | 385 (M+) | CDCl3 3.86(d, J=6Hz, 1H), 4.31 (dABq, J=8Hz, Jab=20Hz, Δν=36Hz, 2H), 5.50(m, 1H), 5.51(d, J=6Hz, 1H), 7.07-7.43(m, 16H) | C24H23N3O2 | | | |
| 98 | CH2Ph-2-Cl | M | chrom (EtOAc: hexane) | 380 mg 39% | | 405 (M+) | CDCl3 2.65(s, 3H), 3.66(d, J=2Hz, 1H), 4.38(ABq, J=20Hz, Δν=72Hz, 2H), 4.94(d, J=2Hz, 1H), 6.9(m, 2H), 7.15-7.46(m, 13H), 7.9(br s, 1H) | C23H20ClN3O2 | 68.06 68.30 | 4.97 5.13 | 10.35 10.01 |
| 99 | CH2Ph-3-Cl | M | chrom | 149 mg 15% | | 405 (M+) | CDCl3 3.92(d, J=7Hz, 1H), 4.4(m, 2H), 5.39(d, J=7Hz, 1H), 5.55(t, J=6Hz, 1H), 7.15-7.43(m, 14H), 8.48(br s, 1H) | C23H20ClN3O2 | 68.08 67.78 | 4.97 5.07 | 10.35 10.46 |
| 100 | CH2Ph-4-Cl | C | EtOAc: hexane | 750 mg 29% | 133-6 | 405 (M+) | CDCl3 3.88(d, J=6Hz, 1H), 4.26 (dABq, J=7Hz, Jab=17Hz, Δν=48Hz, 2H), 5.48(d, J=6Hz, 1H), 5.57(t, J=7Hz, 1H), 6.94-7.43(m, 14H), 8.9 (br s, 1H) | C23H20ClN3O2 | | | |
| 101 | CH(Me)Ph (S) | A | EtOAc: hexane | 182 mg 30% | 124-7 | 405 (M+) | CDCl3 3.89(d, J=5Hz, 1H), 4.27 (dABq, J=6Hz, Jab=12Hz, Δν=42Hz, 2H), 5.48(t, J=6Hz, 1H), 5.50(d, J=5Hz, 1H), 6.98-7.44(m, 14H), 8.52 (br s, 1H) | C23H20ClN3O2 | 68.06 68.22 | 4.97 5.09 | 10.35 10.15 |
| | | A | chrom | 900 mg | | 385 (M+) | CDCl3' 1.32(q, J=9Hz, 3H), 3.90 | C24H23N3O2 | 74.78 | 6.01 | 10.90 |

TABLE I-continued
PHYSICAL CHEMISTRY DATA ON CCK/GASTRIN ANTAGONISTS

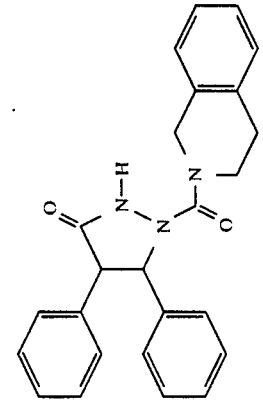

| Example | | Method of Prep. | Solvent of Cryst.[a] | Yield, % | Mp, °C | MS | 1HNMR | Formula | Analysis, % Theory/Found C | H | N |
|---|---|---|---|---|---|---|---|---|---|---|---|
| | (1:1 mixture of diastereomers - each optically active)[d] | | | 34% | | | (dd, J=5Hz, 9Hz, 1H), 4.90(q, J=8Hz, 1H), 5.37(dd, J=9Hz, 36Hz, 1H), 5.45(t, J=5Hz, 1H), 7.0–7.44(m, 15H), 8.53(br s, 1H) | | 75.04 74.89 | 6.10 6.15 | 10.94 10.74 |
| 102 | CH(Me)Ph (R) (1:1 mixture of diastereomers - each optically active)[f] | A | | 172 mg 7% | | 385 (M+) | DMSO[c] 1.20(t, J=6Hz, 3H), 3.60(s, 1H), 3.66(s, ½H), 4.83(m, 1H), 5.43(s, ½H), 5.52(s, ½H), 7.2–7.55(m, 15H), 10.58(s, 1H) | C24H23N3O2 | | | |
| 103 | CH(Me)Ph-4-Br (+/−) (single diastereomer obtained in crystallization)[g] | A | EtOAc: hexane | 670 mg 33% | 145–7 | 463, 465 (M+'s for Br isotopes) | DMSO 1.41(d, J=8Hz, 3H), 3.62(s, 1H), 4.76(m, 1H), 5.42(s, 1H), 7.2–7.62(m, 15H), 10.56(s, 1H) | C24H22BrN3O2 | 62.08 62.27 | 4.78 4.75 | 9.05 8.95 |
| 104 | CH(Me)-1-Naphthyl (R) (c. 3:1 mixture of diastereomers - each optically active)[h] | A | chrom | 137 mg 12% | | 435 (M+) | CDCl3 (peaks for major isomer visible in plot)1.5(d, J=9Hz, 3H), 3.86(d, J=6Hz, 1H), 5.48(d, J=6Hz, 1H), 5.74(m, 1H), 7.06–8.19(m, 19H) | C28H25N3O2 | | | |
| 105 | CH2CH2Ph | A | chrom | 720 mg 30% | | 385 (M+) | CDCl3 2.68(m, 2H), 3.42(m, 2H), 3.86(d, J=6Hz, 1H), 4.94(t, J=5Hz, 1H), 5.27(d, J=6Hz, 1H), 6.95–7.44 (m, 15H) | C24H23N3O2 | 74.78 74.49 | 6.01 6.15 | 10.90 10.74 |
| 106 | CH2CH2Ph-2-Cl | C | chrom | 2.2 g 63% | | 419 (M+) | CDCl3 2.82(m, 2H), 3.45(m, 2H), 3.85(d, J=7Hz, 1H), 5.02(t, J=6Hz, 1H), 5.25(d, J=7Hz, 1H), 6.95–7.4 (m, 14H), 8.58(br s, 1H) | C24H22ClN3O2 | 68.65 68.86 | 5.28 5.36 | 10.01 10.01 |
| 107 | CH2CH2Ph-4-Cl | C | chrom | 1.5 g 66% | | 419 (M+) | CDCl3 2.63(m, 2H), 3.40(m, 2H), 3.86(d, J=8Hz, 1H), 4.83(t, J=6Hz, 1H), 5.22(d, J=8Hz, 1H), 6.88–7.42 (m, 14H), 8.45(br s, 1H) | C24H22ClN3O2 | 68.65 68.84 | 5.28 5.36 | 10.01 9.76 |
| 108 | CH2CH2CH2Ph | D | chrom (EtOAc: hexane) | 239 mg 48% | | 399 (M+) | CDCl3 1.70(pentet, J=7Hz, 2H), 2.48 (t, J=7Hz, 2H), 3.18(m, 2H), 3.89(d, J=6Hz, 1H), 4.92(br t, J=6Hz, 1H), 5.35(d, J=6Hz, 1H), 7.02–7.46(m, 15H), 8.25(br s, 1H) | C25H25N3O2 | 75.16 74.89 | 6.31 6.28 | 10.52 10.27 |

TABLE I-continued
PHYSICAL CHEMISTRY DATA ON CCK/GASTRIN ANTAGONISTS

| Ex. | R1 | R2 | R3 | B | | Mp, °C. | | | | | |
|---|---|---|---|---|---|---|---|---|---|---|---|
| 109 | | | | chrom | 75 mg 4% | 160-6 | 397 (M+) | | CDCl3 2.58–2.82(m, 2H), 3.17–3.48(m, 2H), 3.37–3.48(m, 2H), 3.54–3.62(m, 1H), 3.64(d, J=2, 1H), 4.37(d, J=3.5, 2H), 4.95(d, J=2, 1H), 6.78(m, 1H), 7.02–7.46(m, 13H), 8.18(br s, 1H) | C25H23N3O2 | |

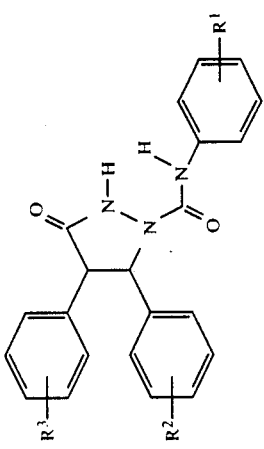

Structure for examples 110–133A below

| Ex. | R1 | R2 | R3 | Meth. Prep. | Solvent of Cryst.ᵃ | Yield, % | Mp, °C. | MS | 1HNMR | Formula | Analysis, % Theory/Found C | H | N |
|---|---|---|---|---|---|---|---|---|---|---|---|---|---|
| 110 | 4-CF3 | 2-Cl | H | A | EtOAc | 185 mg 19% | | 459 (M+) | DMSO 3.57(br s, 1H), 5.72(br s, 1H), 7.14–7.82(m, 13H), 9.72(br s, 1H), 11.01(br s, 1H) | C23H17ClF3N3O2 | 60.07 3.73 9.14 / 59.85 3.80 8.82 | | |
| 111 | 4-CF3 | 3-CN | H | A | triturated with PhMe | 1.80 g 88% | | 450 (M+) | DMSO 3.90(br s, 1H), 5.67(br s, 1H), 7.12–7.98(m, 13H), 9.63(br s, 1H), 10.83(br s, 1H) | C24H17F3N4O2 | 64.00 3.80 12.44 / 64.09 3.98 12.26 | | |
| 112 | 4-CF3 | 3-OMe | H | A | chrom (2X with EtOAc: hexane), then triturated with PhMe: hexane | 160 mg 9% | | 455 (M+) | CDCl3 3.82(s, 3H), 4.03(d, J=7Hz, 1H), 5.51(d, J=7Hz, 1H), 6.92–7.00(m, 3H), 7.14–7.50(m, 10H), ~8.8(br s, 1H) | C24H20F3N3O3 | 63.29 4.43 9.23 / 63.00 4.36 9.03 | | |
| 113 | 4-CF3 | 4-N(Me)2 | H | A | EtOAc: hexane | 95 mg 32% | | 468 (M+) | DMSO 2.90(s, 6H), 3.73(br s, 1H), 5.46(br s, 1H), 6.77(d, J=8Hz, 2H), 7.23–7.40(m, 7H), 7.62(d, J=8Hz, 2H), 7.76(d, J=8Hz, 2H), 9.42(br s, 1H), 10.81(br s, 1H) | C25H23F3N4O2 | 64.10 4.95 11.96 / 64.26 5.18 11.71 | | |
| 114 | 4-Br | 2-Cl | H | A | PhMe, then EtOAc: hexane | 47 mg 10% | | 469, 471 (M+'s for Br isotopes) | DMSO 3.53(br s, 1H), 5.72(br s, 1H), 7.12–7.60(m, 13H), 9.49(br s, 1H), 10.93(br s, 1H) | C22H17BrClN3O2 | 56.13 3.64 8.94 / 56.24 3.62 8.82 | | |
| 115 | 4-Br | 2-OMe | H | A | EtOAc: hexane | 52 mg 17% | | 465, 467 (M+'s for Br isotopes) | CDCl3 3.72(s, 1H), 3.78(s, 3H), 5.50(br s, 1H), 6.87–7.04 (m, 3H), 7.27–7.52(m, 10H), 9.29(br s, 1H) | C23H20BrN3O3 | 59.24 4.32 9.01 / 59.46 4.23 8.90 | | |
| 116 | 4-Br (trans) | 2,3-diCl | H | A | triturated with Et2O, then CH2Cl2: hexane (to give) CH2Cl2 hemisolvate | 1.89 g 69% | | 503, 505 (M+'s), 506, 508 (M+1's for Cl, Br isotopes) | DMSO 3.58(s, 1H), 5.65(s, 1H), 5.70(s, 2H for ½CH2Cl2), 7.28–7.46(m, 12H), 9.43(br s, 1H), 10.91(br s, 1H) | C22H16BrCl2N3O2·½CH2Cl2 | 49.35 3.13 7.67 / 49.60 3.25 7.78 | | |

TABLE I-continued
PHYSICAL CHEMISTRY DATA ON CCK/GASTRIN ANTAGONISTS

| # | | | | | | | | | | | |
|---|---|---|---|---|---|---|---|---|---|---|---|
| 117 | 4-Br (cis) | 2,3-diCl | H | A | CH2Cl2 (2X) | 76 mg 54% | 198–205 | 503, 505, 507(M+'s for Cl, Br isotopes) | DMSO 5.04(d, J=10Hz, 1H), 6.30(m, 1H), 6.72(d, J=7Hz, 2H), 7.00–7.12(m, 3H), 7.30–7.60(m, 7H), 9.31(br s, 1H), 10.70(br s, 1H) | C22H16BrCl2N3O2 | 52.31 3.19 8.32 / 52.59 3.27 8.35 |
| 118 | 4-Br | 3-CONH2 | H | A | CH3CN | 237 mg 45% | 210-3 | 479, 481 (M + 1's for Br isotopes) | DMSO 3.78(s, 1H), 5.55(s, 1H), 7.25–7.59(m, 12H), 7.80 (d, J=8Hz, 1H), 7.94(d, J=24Hz, 2H), 9.28(s, 1H), 10.78(br s, 1H) | C23H19BrN4O3 | 57.63 4.00 11.69 / 57.57 3.96 11.66 |
| 119 | 4-Br | 4-NO2 | H | A | EtOAc: PhMe | 343 mg 60% | | 480, 482 (M+'s for Br isotopes) | DMSO 3.88(br s, 1H), 5.69(br s, 1H), 7.30–7.53(m, 9H), 7.76 (br d, J=7Hz, 2H), 8.31(d, J=8Hz, 2H), 9.39(br s, 1H), 10.93 (br s, 1H) | C22H17BrN4O4 | 54.90 3.56 11.64 / 55.15 3.64 11.55 |
| 120 | 3-CF3, 4-Cl | 2-Cl | H | A | EtOAc: hexane | 604 mg 44% | | 493, 495 (M+'s for Br isotopes) | DMSO 3.58(br s, 1H), 5.72 (br s, 1H), 7.30–7.50(m, 7H), 7.58–7.67(m, 3H), 7.93(d, J=9Hz, 1H), 8.15(br s, 1H), 9.83 (br s, 1H), 11.04(br s, 1H) | C23H16Cl2F3N3O2 | 55.89 3.26 8.50 / 55.85 3.21 8.43 |
| 121 | 4-i-Pr | 2-Cl | H | A | EtOAc: hexane | 514 mg 43% | | 434 (M + 1) | DMSO 1.18(d, J=7Hz, 6H), 2.84(m, J=7Hz, 1H), 3.51(br s, 1H), 5.74(br s, 1H), 7.14–7.64(m, 13H), 9.27(br s, 1H), 10.88(br s, 1H) | C25H24ClN3O2 | 69.20 5.58 9.68 / 69.00 5.55 9.73 |
| 122 | 4-Br | H | 2-Cl | A | EtOAc | 750 mg 43% | 182–2.5 | 470 (M + 1) | DMSO 4.16(br s, 1H), 5.66(br s, 1H), 7.48–7.88(m, 13H), 9.56(br s, 1H), 11.26(br s, 1H) | C22H17BrClN3O2 | 56.13 3.64 8.93 / 56.35 3.62 8.92 |
| 123 | 4-Br | H | 3-OMe | A | EtOAc: hexane | 520 mg 30% | 154–5 | 467 (M+) | CDCl3 3.72(s, 3H), 4.94(d, J=6Hz, 1H), 5.57(d, J=6Hz, 1H), 6.74–6.88(m, 3H), 7.04–7.32(m, 7H), 7.42(br s, 4H), 9.22(br s, 1H) | C23H20BrN3O3 | 59.24 4.32 9.01 / 59.44 4.39 9.06 |
| 124 | 4-Br | H | 3-O-i-Pr | A | Et2O: hexane | 2.24 g 91% | 148–51 | 493, 495 (M+'s for Br isotopes) | CDCl3 1.22(t, J=6Hz, 6H), 3.90(d, J=4.5Hz, 1H), 4.43 (septet, J=6Hz, 1H), 5.58(d, J=4.5Hz, 1H), 6.74–6.82(m, 3H), 7.08(dd, J=2, 9Hz, 2H), 7.19–7.29(m, 5H), 7.36–7.42 (m, 5H) | C25H24BrN3O3 | 60.74 4.89 8.50 / 60.53 4.94 8.70 |
| 125 | 4-Br | H | 3-NO2 | A | CH2Cl2: hexane | 1.32 g 48% | 150–1.5 | 480, 482 (M+'s for Br isotopes) | DMSO 4.05(s, 1H), 5.61(s, 1H), 7.27–7.52(m, 9H), 7.66(t, J=8Hz, 1H), 7.82(d, J=8Hz, 1H), 8.16(d, J=8, 1H), 8.22(s, 1H), 9.34(br s, 1H), 10.95(br s, 1H) | C22H17BrN4O4 | 54.90 3.56 11.64 / 54.63 3.67 11.74 |
| 126 | 4-Br | H | 3-Cl | A | EtOAc: hexane | 232 mg 27% | 142–3 | 470 (M + 1) | CDCl3 4.0(d, J=6Hz, 1H), 5.46(d, J=6Hz, 1H), 6.87(br s, 1H), 7.0–7.12(m, 3H), 7.22–7.54(m, 10H), 8.78(br s, 1H) | C22H17BrClN3O2 | 56.13 3.64 8.93 / 56.21 3.76 8.84 |
| 127 | 4-Br | H | 3-Br | A | chrom, then triturated with Et2O: | 128 mg 17% | | 515, 517 (M+'s), 516 (M + 1 | CDCl3 3.94(brd, J=4Hz, 1H), 5.46(brd, J=4Hz, 1H), 7.04–7.44(m, 15H) | C22H17Br2N3O2 | 51.29 3.33 8.16 / 51.66 3.60 7.88 |

TABLE I-continued
PHYSICAL CHEMISTRY DATA ON CCK/GASTRIN ANTAGONISTS

| Ex. | R | Ar1 | Ar2 | Meth. Prep. | Solvent of Cryst.a | Yield, % | Mp, °C | MS | 1HNMR | Formula | Analysis, % Theory/Found C | H | N |
|---|---|---|---|---|---|---|---|---|---|---|---|---|---|
| 128 | 4-Br | H | 4-OMe | A | hexane chrom (EtOAc), then triturated with hexane | 296 mg 34% | | 467 (M+) for Br isotopes | CDCl3 3.78(s, 3H), 3.95(d, J=6Hz, 1H), 5.49(d, J=6Hz, 1H), 6.85(d, J=12Hz, 2H), 7.0-7.18(m, 5H), 7.24-7.5(m, 7H), 9.1(br s, 1H) | C23H20BrN3O3 | 59.24 59.30 | 4.32 4.53 | 9.01 8.78 |
| 129 | 4-Br | H | 4-Cl | A | triturated with Et2O | 1.92 g 82% | 172-4.5 | 469, 471, 473 (M+'s), 470 (M+1 for Cl, Br isotopes) | DMSO 3.78(s, 1H), 5.49(s, 1H), 7.28-7.50(m, 13H), 9.22 (br s, 1H), 10.84(br s, 1H) | C22H17ClBrN3O2 | 56.13 56.03 | 3.64 3.57 | 8.93 9.02 |
| 130 | 4-CF3 | H | 2-Cl | A | triturated with EtOAc: hexane | 260 mg 38% | 178-9 | 459 (M+) | CDCl3 4.4(d, J=6Hz, 1H), 5.58(d, J=6Hz, 1H), 7.2-7.54 (m, 13H), 7.64(br s, 1H), 9.48 (br s, 1H) | C23H17ClF3N3O2 | 60.07 60.07 | 3.73 3.77 | 9.14 9.18 |
| 131 | 3-CF3, 4-Cl | H | 2-Cl | A | triturated with EtOAc: hexane | 250 mg 34% | 109-10 | 493 (M+) | CDCl3 4.38(d, J=6Hz, 1H), 5.6(d, J=6Hz, 1H), 7.16-7.66 (m, 12H), 7.86(br s, 1H), 9.58 (br s, 1H) | C23H16Cl2F3N3O2 | 55.89 55.60 | 3.26 3.24 | 8.50 8.45 |
| 132 | 4-i-Pr | H | 2-Cl | A | EtOAc: hexane | 200 mg 31% | 226-7 | 433 (M+) | DMSO 1.16(d, J=7Hz, 6H), 2.82(m, 1H), 3.92(br s, 1H), 5.46(br s, 1H), 7.12(d, J=12Hz, 2H), 7.28-7.64(m, 11H), 9.14(br s, 1H), 10.98(br s, 1H) | C25H24ClN3O2 | 69.20 69.45 | 5.57 5.60 | 9.68 9.68 |
| 133 | 4-Br (trans) | 2-Cl | 2-Cl | A | EtOAc: hexane | 4.32 g, 88% | | 505 (M+) | DMSO 4.02(br s, 1H), 5.75(br s, 1H), 7.28-7.58(m, 12H), 9.41(br s, 1H), 11.06(br s, 1H) | C22H16BrCl2N3O2 | 52.30 52.07 | 3.19 3.27 | 8.32 8.09 |
| 133A | 4-Br (cis) | 2-Cl | 2-Cl | A (THF) | EtOAc: hexane | 113 mg 48% | | 505 (M+) | DMSO 5.26(d, J=8Hz, 1H), 6.20(br s, 1H), 6.36(d, J=9Hz, 1H), 6.85(t, J=9Hz, 1H), 7.06-7.70(m, 10H), 9.34(br s, 1H), 10.74(br s, 1H) | C22H16BrCl2N3O2 | 52.31 52.23 | 3.19 3.32 | 8.32 8.47 |
| 134 | 4-Br | Ph | 1-Naphthyl | A | Et2O: hexane | 1.48 g 61% | 187-9 | 486, 488 (M+1's for Br | CDCl3 4.70(d, J=6Hz, 1H), 5.59 (d, J=6Hz, 1H), 6.97(d, J=9Hz, 2H), 7.15-7.52(m, 12H), 7.70– | C26H20BrN3O2 | 64.21 64.02 | 4.15 4.20 | 8.64 8.61 |

TABLE I-continued
PHYSICAL CHEMISTRY DATA ON CCK/GASTRIN ANTAGONISTS

| 135 | 4-Br | 3-Pyridyl | Ph | A | EtOAc (2X), then chrom, then EtOAc | 848 mg 24% | 184–87.5 87.5 | isotopes) 437, 439 (M + 1's for Br isotopes) | 7.88(m, 3H), 9.10(br s, 1H) DMSO 3.84(s, 1H), 5.56(s, 1H), 7.23–7.46(m, 10H), 7.83(d, J=8Hz, 1H), 8.53(dd, J=1.1, 4.5Hz, 1H), 8.65(d, J=1.7Hz, 1H), 9.28 (s, 1H), 10.86(br s, 1H) | qC21H17BrN4O2 | 57.68 57.74 | 3.92 3.99 | 12.81 13.07 |

[a] Includes other methods of purification such as chromatography (chrom), trituration, and precipitation, as indicated. If only solvents are given, compound was purified by recrystallization from those solvents. For other methods of purification, solvents used follow in parentheses.
[b] After recrystallization from EtOAc:hexane.
[c] Purified by extraction into 1N NaOH, followed by acidification with 1N HCl and extraction into organic solvent (Et2O or EtOAc). Evaporation of solvent gave material homogeneous by TLC and of satisfactory purity.
[d] Prepared using S-(−)-α-methylbenzylisocyanate.
[e] All splitting patterns reported are those apparent upon visual inspection of plot, and reflect a combination of true proton-proton magnetic couplings, and multiplicity due to presence of a mixture of two diasteromers.
[f] Prepared using R-(+)-α-methylbenzylisocyanate.
[g] Prepared using (±)-4-bromo-α-methylbenzylisocyanate.
[h] Prepared using (R)-(−)-1-(1-naphthyl)ethylisocyanate.

EXAMPLE 136

1-[(2-Naphthyl)aminothiocarbonyl]-4,5-diphenyl-3-pyrazolidinone. [Method G].

2-Aminonaphthalene (2.95 g, 20.6 mmol) was dissolved in 230 mL CHCl₃ under nitrogen. Triethylamine (11.5 mL, 8.35 g, 82.5 mmol, 4.00 eq) was added and the mixture was cooled in an ice bath. Thiophosgene (3.30 mL, 43.3 mmol, 2.0 eq), dissolved in 90 mL CHCl₃, was added slowly over 1 hr. Stirring was continued for 2 hr at room temperature, then the mixture was partitioned between H₂O and CHCl₃. The organic phase was separated, washed with H₂O and two times with 1.0N HCl, then dripped through Na₂SO₄ to remove water and evaporated in vacuo to yield 4.29 g (>100%) of a brown oil which solidified. NMR indicated the desired 2-naphthylisothiocyanate and contaminants: $^1$H NMR (CDCl₃) 7.30–7.85 (m, 7H).

4,5-Diphenyl-3-pyrazolidinone (1.00 g, 4.20 mmol) was dissolved in 10 mL THF under nitrogen and a solution of crude 2-naphthylisothiocyanate (obtained above; 0.93 g, c. 5.0 mmol, c. 1.2 eq) in 10 mL THF was added. After stirring overnight, TLC indicated the presence of unreacted pyrazolidinone, so more 2-naphthylisothiocyanate (0.39 g, c. 0.50 eq) was added in THF. After stirring an additional 1 hr, TLC still indicated some pyrazolidinone. After removal of solvent in vacuo, the residue was partially purified on two sequential silica columns (EtOAc:hexane with 0.5% HOAc). The material so obtained was dissolved in CHCl₃ and extracted three times with pH 10 buffer. The combined aqueous extracts were acidified with 1.0N HCl and then extracted three times with Et₂O. The organic extracts were combined, dripped through Na₂SO₄ to remove water, and evaporated in vacuo to obtain 0.60 g of material, which TLC indicated still contained impurities. The entire extractive procedure was then repeated (using CH₂Cl₂ as the organic phase throughout), to afford 311 mg (17%) of a pale yellow foam:

$^1$H NMR (CDCl₃) δ 4.11 (d, J=5 Hz, 1H), 5.73 (d, J=5 Hz, 1H), 7.26–7.56 (m, 13H), 7.67–7.82 (m, 4H), MS 423 (M+); titration p$K_a$ 5.8. Analysis for C₂₆H₂₁N₃OS: calculated C 73.73, H 5.00, N 9.92; found C 73.75, H 5.13, N 9.97.

TABLE II
PHYSICAL CHEMISTRY DATA ON CCK/GASTRIN ANTAGONISTS

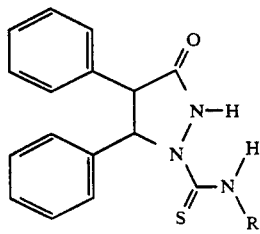

| Ex. | R | Method of Prep. | Solvent of Cryst.$^a$ | Yield, % | Mp, °C. | MS | 1HNMR | Formula | Analysis, % Theory/Found C | H | N |
|---|---|---|---|---|---|---|---|---|---|---|---|
| 137 | 3-Quinolinyl | G | triturated with PhMe | 1.23 g 69% | | 424, 425 (M+, M + 1) | DMSO 3.99(s, 1H), 6.18(br s, 1H), 7.12–7.52(m, 10H), 7.51(td, J=15, 2Hz, 1H), 7.60 (td, J=15, 2Hz, 1H), 7.98(t, J=15Hz, 2H), 8.44(s, 1H), 8.98(d, J=3Hz, 1H), 10.22(br s, 1H), 11.96(br s, 1H) | C25H20N4OS | 70.73 70.52 | 4.75 4.86 | 13.20 12.98 |
| 138 | CH2Ph-3,4-diCl | G | chrom (EtOAc: hexane + HOAc) | 1.38 g 69% | | 456, 458 (M+'s for Br isotopes) | CDCl3 4.00(d, J=5Hz, 1H), 4.48(dd, J=5, 17Hz, 1H), 4.76 (dd, J=7, 17Hz, 1H), 5.65(d, J=5Hz, 1H), 6.05(br s, 1H), 6.87(dd, J=2, 9Hz, 1H), 7.07–7.46(m, 12H), 9.45(br s, 1H) | C23H19Cl2N3OS | 60.53 60.30 | 4.20 4.33 | 9.21 8.95 |

$^a$Includes other methods of purification such as chromatography (chrom), trituration, and precipitation, as indicated. If only solvents are given, compound was purified by recrystallization from those solvents. For other methods of purification, solvents used follow in parentheses.

PREPARATION 1

(R)-α-Methylbenzylphenylcarbonate.

(R)-α-Methylbenzyl alcohol (4.34 g, 35.5 mmol) was dissolved in 120 mL CH₂Cl₂ under nitrogen and pyridine (4.31 mL, 1.5 eq) was added. The mixture was cooled in an ice bath and a solution of phenyl chloroformate in 30 mL CH₂Cl₂ slowly added. After addition, the ice bath was removed and stirring continued overnight at room temperature. The mixture was partitioned between CH₂Cl₂ and 1.0N HCl, then the organic layer separated, dripped through Na₂SO₄ to remove water, and the solvent evaporated in vacuo to obtain 8.34 g of an oil, which was used without further purification (97% crude yield):

$^1$H NMR (CDCl₃) δ 1.69 (d, J=7 Hz, 3H), 5.83 (q, J=7 Hz, 1H), 7.14–7.46 (m, 10H); MS 242 (M+);[α]$_D$=+119.6°, [α]$_{365}$=+428.8° (c=1.02, MeOH). Analysis for C₁₅H₁₄O₃: calculated C 74.36, H 5.82; found C 74.06, H 5.98.

EXAMPLE 139A/139B

Diastereomers A and B of
1-[((R)-α-Methylbenzyl)oxycarbonyl]trans-4,5-diphenyl-3-pyrazolidinone.

(+)-trans-4,5-Diphenyl-3-pyrazolidinone (8.13 g, 34.2 mmol) was dissolved in 150 mL THF under nitrogen, cooled in an ice bath, and 1.43 g NaH (60% in mineral oil; hydride content 0.86 g, 35.7 mmol, 1.05 eq) was added. The mixture was stirred for 15 min at ice bath temperature and 30 min at room temperature. A solution of (R)-α-methylbenzylphenylcarbonate [from Preparation 1] (8.25 g, 34.1 mmol, 1.00 eq) in THF was then added over 10 min and the mixture stirred a further 40 min. After partitioning between Et$_2$O and 1.0N HCl, the organic phase was separated, and the aqueous phase extracted a second time with Et$_2$O. The organic extracts were combined, dripped through Na$_2$SO$_4$ to remove water, and evaporated to provide 17.45 g of a crude mixture of the title products. Preliminary purification (without separation of diastereomers) was achieved on two sequential silica columns (EtOAc:hexane). Final purification and separation of diastereomers A and B was accomplished via HPLC (Waters RCM 1.2.3 system; 3 piggybacked Nova C18 columns, each 40×100 mm, 6μM particles; flow rate=45 mL/min (c. 1100 psi); UV detection at 245 nm/1.0 AUFS; eluent 64% MeOH:H$_2$O with 2.5% HOAc; loading c. 50-60 mg/injection). Three fractions were collected: the first was highly enriched in diastereomer A, the second contained a mixture of A and B (which was recycled), and the third was highly enriched in diastereomer B. The first fractions from various runs were combined, evaporated, and the residue lyophilized to yield diastereomer A. Processing of the third fractions from various runs in a similar fashion yielded diastereomer B. The diastereomeric purity of A and B were determined on analytical HPLC (Nova C18 column; eluent 70% MeOH:H$_2$O with 1% HOAc at 1500 psi; UV detection at 254 nm), and were typically in the range 95-100%.

Diastereomer A: $^1$H NMR (CDCl$_3$) δ 1.48 (d, J=8 Hz, 3H), 3.88 (d, J=6 Hz, 1H), 5.34 (d, J=6 Hz, 1H), 5.81 (q, J=8 Hz, 1H), 7.03 (m, 1H), 7.15-7.42 (m, 14H), 8.08 (br s, 1H), MS 386 (M+); titration pK$_a$ 8.7; [α]$_D$=−23.1°, [α]$_{365}$=−71.0° (c=0.99, MeOH). Analysis for C$_{24}$H$_{22}$N$_2$O$_3$: calculated C 74.59, H 5.74, N 7.25; found C 74.52, H 5.97, N 7.24. Diastereomer B: $^1$H NMR (CDCl$_3$) δ 1.42 (d, J=7 Hz, 3H), 3.88 (d, J=5 Hz, 1H), 5.34 (s, 1H), 5.80 (q, J=7 Hz, 1H), 7.14-7.43 (m, 15H), 8.30 (br s, 1H), MS 386 (M+); titration pK$_a$ 8.6; [α]$_D$=−18.7°, [α]$_{365}$=−122.2° (c=1.01, MeOH). Analysis for C$_{24}$H$_{22}$N$_2$O$_3$: calculated C 74.59, H 5.74, N 7.25; found C 74.79, H 5.84, N 7.22.

PREPARATION 2

(+)-trans-4,5-Diphenyl-3-pyrazolidinone.

A thick-walled glass hydrogenation tube was charged with diastereomer B of 1-[((R)-α-methylbenzyl)oxycarbonyl]-trans-4,5-diphenyl-3-pyrazolidinone [from Example 139A/139B] (226 mg, 0.586 mmol), 15.0 mL THF and 5% Pd/C catalyst (112 mg) and was shaken on a Parr apparatus under an atmosphere of hydrogen at c. 50 psi pressure for 15.5 hr. The catalyst was filtered off using Celite and washed with THF. The filtrate was evaporated in vacuo to obtain 134 mg (96%) of a white foam:

$^1$H NMR (CDCl$_3$) δ 3.99 (d, J=11 Hz, 1H), 4.66 (br s, 1H), 4.74 (d, J=11 Hz, 1H), 7.20-7.39 (m, 10H), 8.63 (br s, 1H).

PREPARATION 3

(−)-trans-4,5-Diphenyl-3-pyrazolidinone.

Diastereomer A of 1-[((R)-α-methylbenzyl)oxycarbonyl]-trans-4,5-diphenyl-3-pyrazolidinone [from Example 139A/139B] (261 mg, 0.677 mmol) was subjected to hydrogenolysis (17 mL THF, 128 mg 5% Pd/C) and workup as described in Preparation 2 to obtain 154 mg (96%) of a white foam:

$^1$H NMR (CDCl$_3$) δ 4.01 (d, J=11 Hz, 1H), 4.38 (br s, 1H), 5.81 (br s, 1H), 7.18-7.41 (m, 10H); [α]$_D$=−76°, [α]$_{365}$=−278° (c=1.08, CHCl$_3$).

EXAMPLE 140

(−)-trans-1-[(4-Bromophenyl)aminocarbonyl]-4,5-diphenyl-3-pyrazolidinone.

(+)-trans-4,5-Diphenyl-3-pyrazolidinone [from Preparation 2] (70.7 mg, 0.297 mmol) was dissolved in 1.0 mL THF under an argon atmosphere and treated with a solution of 4-bromophenylisocyanate (67.9 mg, 0.343 mmol, 1.15 eq) in 1.0 mL THF. The mixture was stirred for 45 min, then the solvents removed in vacuo. The product was initially purified by chromatography (EtOAc:toluene) to provide 90.4 mg of material, in which impurities were still apparent by NMR. This was dissolved in toluene and hexane added until a precipitate appeared. Solvents were carefully removed by pipette and the remaining solid dried on a vacuum pump, giving 77.3 mg (60%) of a white solid:

$^1$H NMR (CDCl$_3$) δ 4.01 (d, J=7 Hz, 1H), 5.52 (d, J=7 Hz, 1H), 6.90-7.50 (m, 15H), 8.60 (br s, 1H), MS 435, 437 (M+'s for Br isotopes); [α]$_D$=−39°, [α]$_{365}$=−293° (c=1.26, CHCl$_3$). Analysis for C$_{22}$H$_{18}$BrN$_3$O$_2$: calculated C 60.56, H 4.16, N 9.63; found C 61.43, H 4.29, N 9.58. Enantiomeric excess (ee) 95.1%, based on HPLC assay of diastereomeric purity of precursor diastereomer B from Example 139A/139B.

EXAMPLE 141

(+)-trans-1-[(4-Bromophenyl)aminocarbonyl]-4,5-diphenyl-3-pyrazolidinone.

(−)-trans-4,5-Diphenyl-3-pyrazolidinone [from Preparation 3] (82.9 mg, 0.348 mmol) was dissolved in 1.0 mL THF under an argon atmosphere and treated with a solution of 4-bromophenylisocyanate (76.8 mg, 0.388 mmol, 1.11 eq) in 1.0 mL THF. The mixture was stirred for 30 min, then the solvents removed in vacuo. The product was initially purified by chromatography (33−>66% EtOAc:toluene gradient) to provide 51.6 mg of material, in which impurities were still apparent by NMR. This was triturated with hexane, then the resulting solid recrystallized from CH$_2$Cl$_2$:toluene:hexane. Careful removal of solvents via pipette and drying on a vacuum pump yielded 20.8 mg (14%) of a white solid: $^1$H NMR (CDCl$_3$) δ 4.02 (d, J=7 Hz, 1H), 5.52 (d, J=7 Hz, 1H), 6.90-7.50 (m, 15H), 8.60 (br s, 1H), MS 435, 437 (M+'s for Br isotopes); [α]$_D$=+40°, [α]$_{365}$=+299° (c=0.88, CHCl$_3$). Analysis for C$_{22}$H$_{18}$BrN$_3$O$_2$: calculated C 60.56, H 4.16, N 9.63; found C 61.93, H 4.43, N 9.37. Enantiomeric excess (ee) 100%, based on HPLC assay of diastereomeric purity of precursor diastereomer A from Example 139A/139B.

EXAMPLE 142

(+)-trans-1-[(4-Chloro-3-trifluoromethylphenyl)-aminothiocarbonyl]-4,5-diphenyl-3-pyrazolidinone.

(+)-trans-4,5-Diphenyl-3-pyrazolidinone [from Preparation 2] (134 mg, 0.561 mmol) was dissolved in 8.0 mL THF under nitrogen and a solution of 4-chloro-3-trifluoromethylphenylisothiocyanate (137 mg, 0.578 mmol, 1.03 eq) in 2 mL THF was added. The mixture was stirred for 12 hr and then the solvent removed in vacuo. The residue was first purified on two sequential silica columns (EtOAc:hexane with 0.5% HOAc). The partially purified material so obtained (155 mg) was dissolved in $CH_2Cl_2$ and extracted three times with pH 10 buffer. The aqueous extracts were combined, acidified with 1.0N HCl, and extracted three times with $CH_2Cl_2$. The organic extracts were combined, dripped through $Na_2SO_4$ to remove water, and evaporated in vacuo to give 93.5 mg (35%) of the product as a pale yellow foam:

$^1$H NMR (CDCl$_3$) δ 4.10 (d, J=5 Hz, 1H), 5.74 (d, J=5 Hz, 1H), 7.35-7.60 (m, 15H); MS 475 (M+);[α]$_D$=+32°, [α]$_{365}$=−116° (c=1.06, CHCl$_3$). Analysis for $C_{23}H_{17}ClF_3N_3OS$: calculated C 58.05, H 3.60, N 8.83; found C 57.86, H 3.79, N 8.69. Enantiomeric excess (ee) 98.6%, based on HPLC assay of diastereomeric purity of precursor diastereomer B from Example 139A/139B.

EXAMPLE 143

(−)-trans-1-[(4-Chloro-3-trifluoromethylphenyl)-aminothiocarbonyl]-4,5-diphenyl-3-pyrazolidinone.

(−)-trans-4,5-Diphenyl-3-pyrazolidinone [from Preparation 3] (147 mg, 0.617 mmol) was dissolved in 8.0 mL THF under nitrogen and treated with a solution of 4-chloro-3-trifluoromethylphenylisothiocyanate (160 mg, 0.673 mmol, 1.09 eq) in 3 mL THF. The mixture was stirred for 1.5 hr and the solvent then removed in vacuo. The product was stirred for 1.5 hr and the solvent then removed in vacuo. The product was purified as for Example 142, except that the initial chromatographic steps were omitted, and the entire extractive procedure was repeated a second time, to yield 145 mg (49%) of a pale yellow foam:

$^1$H NMR (CDCl$_3$) δ 4.14 (d, J=5 Hz, 1H), 5.74 (d, J=5 Hz, 1H), 7.35-7.60 (m, 15H); MS 475 (M+); [α]$_D$=−28°, [α]$_{365}$=+128° (c=1.15, CHCl$_3$). Analysis for $C_{23}H_{17}ClF_3N_3OS$: calculated C 58.05, H 3.60, N 8.83; found C 57.77, H 3.67, N 8.64. Enantiomeric excess (ee) 97.2%, based on HPLC assay of diastereomeric purity of precursor diastereomer A from Example 139A/139B.

TEST PROCEDURES FOR CCK AND GASTRIN RECEPTOR BINDING (IC$_{50}$)

Brain

Brain CCK receptor binding was performed using mouse brain membranes according to the method of Chang and Lotti (*Proc. Natl. Acad. Sci.* 83: 4923–4926, 1986). Male .CF-1 mice, 23–25 g were sacrificed by cervical dislocation, the forebrain removed and placed in ice cold 50 mM Tris buffer, pH 7.4. The tissue was homogenized in 100 volumes of the Tris buffer with a Brinkman Polytron or Tekmar Tissumizer and then centrifuged at 40,000 g for 10 min. Pellets were resuspended in Tris buffer, centrifuged as above and then resuspended in 100 volumes of assay buffer, pH 6.5 (20 mM N-2-hydroxyethyl-piperazine-N'-2-ethane sulfonic acid (HEPES), 1 mM ethylene glycol bis(2-aminoethyl ether-N,N,N',N'-tetraacetic acid) (EGTA), 5 mM MgCl$_2$, 130 mM NaCl, and 0.25 mg/ml bacitracin). The binding assay consisted of 50 μL of compound (or buffer for total binding), 50 μL of $^{125}$I-CCK-8 sulfate (20 pM) (Amersham IM-159), 200 μL of assay buffer and 200 μL of homogenate (80–120 μg protein). The samples were incubated at room temperature (25°) for 2 hours, and they were then filtered through GF/B glass fiber filters (soaked in wash buffer for 2 hours before use) using a 48 well Brandel cell harvester designed for receptor binding. The filters were washed twice with 3 ml of 50 mM Tris buffer, pH 7.4, containing 0.01% BSA and then counted for radioactivity in plastic tubes with a Micromedic 10/600 automatic gamma counter.

Compounds were dissolved in dimethyl sulfoxide (DMSO) at a concentration of 10 mM and then further diluted with assay buffer. The concentration of DMSO in the incubation was 0.1% or less and had no effect on the assay at that level. IC-50 values of displacement curves were determined using 7 concentrations of compound and were calculated using the ALLFIT computer program of DeLean, Munson and Rodbard (*Am. J. Physiol.* 235: E97–E102, 1978). Non-specific binding was determined as the displacement of the radioligand by 100 nM CCK-8 sulfate.

Pancreas

Binding to peripheral type CCK receptors in rat pancreas was done according to the method of Chang et al. (*Mol. Pharmacol.* 30: 212–217, 1986) using $^3$H-L364,718. Pancreas was obtained from male Sprague-Dawley rats, 150–200 g, after decapitation, and dissected free from adipose and connective tissue. The tissue was homogenized in 30 volumes of 50 mM Tris buffer, pH 7.4 and centrifuged at 40,000 g for 10 min. The tissue pellet was washed by resuspension and centrifugation as described above. The final pellet was suspended in 500 volumes of assay buffer (50 mM Tris buffer, pH 7.4, 5 mM MgCl$_2$, 0.14 mg/ml bacitracin, and 5 mM dithiothreitol) to give a protein concentration of 30–60 μg/200 μl. Reagent volumes for the assay were the same as those used for CCK binding to brain membranes. Tritium labeled L-364,718 (Dupont NEN, NET-971) was used as the ligand at a concentration of 0.4–0.6 nM. The samples were incubated 1 hour at room temperature and then filtered as described for the CCK-brain receptor. Scintillation cocktail was added to the filters which were counted for radioactivity using a Micromedic Taurus automatic liquid scintillation counter.

Compound samples were prepared and IC-50 values were determined as described for the CCK-brain experiments. Non-specific binding was that amount left bound to the filters after adding 100 nM L-364,718.

Gastric Mucosa

The method used for gastrin binding to guinea pig stomach mucosal membranes was similar to that described by Takeuchi, Speir and Johnson (*Am. J. Physiol.* 237(3): E284–E294, 1979). Guinea pig stomach fundus was obtained from male Hartley guinea pigs, 300–350 g, and the mucosa was scraped off with a glass slide. The mucosa was homogenized in 50 mM Tris buffer, pH 7.4, containing 1 mM phenylmethanesulfonyl fluoride using a Dounce glass homogenizer, and the suspension was centrifuged at 40,000 g for 10 min. The resulting pellet was resuspended and centrifuged once more, the final pellet was then suspended in 100 ml assay buffer per 1 guinea pig stomach to give a protein concentration of 200–300 μg/200 μl. The assay buffer consisted of 50 mM Tris buffer, pH 7.4, 5 mM $MgCl_2$, 0.14 mg/ml bacitracin, and 1 μg/ml each of leupeptin, chymostatin, aprotinin and pepstatin. Reagent volumes for the assay were the same as those used for CCK binding to brain membranes. The radioactive ligand was 20 pM $^{125}I$-gastrin I, from DuPont NEN (NEX-176). The samples were incubated 3 hours at room temperature and filtered and counted as described for CCK binding to brain membranes. Compound samples were prepared and IC-50 values were determined as described for the CCK-brain receptor binding. Non-specific binding was determined using 100 nM gastrin I (human synthetic from Sigma Chemical Co.).

Table III below summarizes representative CCK and gastrin-binding tests results for exemplified compounds in accordance with this invention.

TABLE III

CCK and Gastrin Receptor Binding Data

| Compound of Example No. | $IC_{50}$, μM, or Percent Inhibition (at 1 or 10 μM) | | |
|---|---|---|---|
| | Brain | Pancreas | Gastrin |
| 1 | 0.022 | 0.19 | 0.15 |
| 2 | 0.29 | 14(10) | |
| 3 | 0.054 | 34(10) | 1.1 |
| 4 | 0.39 | 78(10) | |
| 5 | 77(10) | 18(10) | |
| 6 | 4.4 | 15(10) | |
| 7 | 1.1 | 81(10) | |
| 8 | 34(10) | 2(10) | |
| 9 | 3.7 | 33(10) | |
| 10 | 57(10) | 4(10) | |
| 11 | 67(10) | | |
| 12 | 0.34 (O-) | 64(10) | |
| | 1.9 (N-) | 55(10) | |
| 13 | 67(10) | | |
| 14 | 2.6 | 60(10) | |
| 15 | 69(10) | 10(10) | |
| 16 | 0.044 | 62(10) | 0.42 |
| 17 | 0.52 | 6(10) | |
| 18 | 0.093 | 22(10) | |
| 19 | 68(10) | 36(10) | |
| 20 | 0.031 | 11.6 | 0.49 |
| 21 | 0.057 | 77(10) | |
| 22 | 42(1) | 27(10) | |
| 23 | 0.49 | 23(10) | |
| 24 | 0.15 | 45(10) | |
| 25 | 0.21 | 14(10) | |
| 26 | 0.075 | 47(10) | |
| 27 | 0.23 | 60(10) | |
| 28 | 0.44 | 55(10) | |
| 29 | 0.025 | 47(10) | 0.26 |
| 30 | 0.031 | 49(10) | 0.35 |
| 31 | 54(1) | 71(10) | |
| 32 | 42(1) | 69(10) | |
| 33 | 0.34 | 20(10) | |
| 34 | 1.5 | 12(10) | |
| 35 | 0.39 | 48(10) | |
| 36 | 0.45 | 33(10) | |
| 37 | 82(1) | 75(10) | |
| 38 | 0.056 | 53(10) | 0.24 |
| 39 | 0.33 | 52(10) | |
| 40 | 0.75 | 38(10) | |
| 41 | 57(10) | 21(10) | |
| 42 | 0.78 | 37(10) | |
| 43 | 0.23 | 24(10) | |
| 44 | 0.26 | 67(10) | |
| 45 | 0.022 | 0.16 | |
| 46 | 0.042 | 1.2 | 0.21 |
| 47 | 0.39 | 51(10) | |
| 48 | 0.080 | 98(10) | |
| 49 | 0.043 | 40(10) | 0.25 |
| 50 | 0.013 | 87(10) | 0.081 |

TABLE III-continued

CCK and Gastrin Receptor Binding Data

| Compound of Example No. | $IC_{50}$, μM, or Percent Inhibition (at 1 or 10 μM) | | |
|---|---|---|---|
| | Brain | Pancreas | Gastrin |
| 51 | 18(1) | 25(10) | |
| 52 | 60(1) | 21(10) | |
| 53 | 1.2 | 17(10) | |
| 54 | 1.15 | 53(10) | |
| 55 | 0.60 | 47(10) | |
| 56 | 25(1) | 15(10) | |
| 57 | 1.0 | 45(10) | |
| 58 | 10(1) | 85(10) | |
| 59 | 44(1) | 75(10) | |
| 60 | 34(10) | 37(10) | |
| 61 | 56(10) | 78(10) | |
| 62 | 2.2 | 37(10) | |
| 63 | 0.51 | 0.075 | |
| 64 | 5.3 | 34(1) | |
| 65 | 50(10) | 37(10) | |
| 66 | 40(10) | 23(10) | |
| 67 | 46(10) | | |
| 68 | 4.3 | 70(10) | |
| 69 | 0.5 | 12(10) | |
| 70 | 13(1) | 36(10) | |
| 71 | 1.2 | 39(10) | |
| 72 | 88(10) | 22(10) | |
| 73 | 16(10) | 20(10) | |
| 74 | 23(10) | 15(10) | |
| 75 | 60(10) | 40(10) | |
| 76 | 55(10) | 4(10) | |
| 77 | 56(10) | 20(10) | |
| 78 | 1.8 | 49(10) | |
| 79 | 43(10) | 9(10) | |
| 80 | 5.2 | 9(10) | |
| 81 | 95(10) | 59(10) | |
| 82 | 23(10) | | |
| 83 | 37(1) | 12(10) | |
| 84 | 70(10) | 26(10) | |
| 85 | 78(10) | 19(10) | |
| 86 | 1.1 | 58(10) | |
| 87 | 47(10) | 23(10) | |
| 88 | 40(10) | 37(10) | |
| 89 | 34(10) | 21(10) | |
| 90 | 45(1) | 63(10) | |
| 91 | 0.010 | 94(10) | 0.062 |
| 92 | 0.064 | 88(10) | 0.16 |
| 93 | 0.29 | 75(10) | 0.66 |
| 9 | 50(10) | | |
| 95 | 55(10) | 18(10) | |
| 96 | 42(10) | 13(10) | |
| 97 | 42(10) | | |
| 98 | 74(10) | 33(10) | |
| 99 | 3.3 | 86(10) | |
| 100 | 2.2 | 78(10) | |
| 101 | 1.3 | 7(10) | |
| 102 | 4.7 | 11(10) | |
| 103 | 0.87 | 78(10) | |
| 104 | 0.9 | 47(10) | |
| 105 | 0.49 | 43(10) | |
| 106 | 0.19 | 78(10) | 0.87 |
| 107 | 86(10) | 61(10) | |
| 108 | 1.3 | 87(10) | |
| 109 | 6.0 | 11(10) | |
| 110 | 0.007 | 47(10) | 0.13 |
| 111 | 0.020 | 35(10) | 0.61 |
| 112 | 0.072 | 42(10) | 1.4 |
| 113 | 25(1) | 21(10) | |
| 114 | 0.020 | 38(10) | 0.36 |
| 115 | 0.15 | 53(10) | 0.32 |
| 116 | 0.031 | 80(10) | 0.23 |
| 117 | 0.40 | 64(10) | 1.0 |
| 118 | 0.36 | 41(10) | 5.2 |
| 119 | 1.2 | 64(10) | |
| 120 | 0.016 | 87(10) | 0.12 |
| 121 | 0.014 | 26(10) | 0.12 |
| 122 | 0.015 | 8.6 | 0.22 |
| 123 | 0.068 | 23(10) | 0.69 |
| 124 | 0.15 | 36(10) | 0.73 |
| 125 | 0.10 | 42(10) | 0.59 |
| 126 | 0.011 | 59(10) | 0.21 |
| 127 | 0.032 | 73(10) | 0.21 |

TABLE III-continued

| CCK and Gastrin Receptor Binding Data | | | |
|---|---|---|---|
| Compound of Example No. | $IC_{50}$, μM, or Percent Inhibition (at 1 or 10 μM) | | |
| | Brain | Pancreas | Gastrin |
| 128 | 0.49 | 39(10) | |
| 129 | 0.16 | 69(10) | 0.86 |
| 130 | 0.012 | 42(10) | 0.10 |
| 131 | 0.012 | 61(10) | 0.062 |
| 132 | 0.008 | 48(10) | 0.070 |
| 133 | 0.006 | 7.9 | 0.025 |
| 133A | 0.36 | 55(10) | 1.5 |
| 134 | 0.033 | 75(10) | 0.093 |
| 135 | 0.14 | 18(10) | 1.7 |
| 136 | | 0.16 | |
| 137 | | 0.032 | |
| 138 | | 0.069 | |
| 140 | 0.37 | | |
| 141 | 0.016 | | |
| 142 | | | 0.017 |
| 143 | | | 0.81 |

We claim:

1. A pharmaceutical formulation comprising as an active ingredient an effective amount of a compound of A compound of the formula

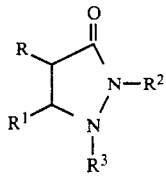      I wherein

R and $R^1$ are independently hydrogen, $C_1$-$C_6$ alkyl, phenyl, benzyl, naphthyl, pyridyl or substituted phenyl having 1, 2, or 3 substituents selected from the group consisting of $C_1$-$C_6$ alkyl, $C_1$-$C_6$ alkoxy, $C_1$-$C_6$ alkylthio, halo, trifluoromethyl, phenyl, phenoxy, phenyl($C_1$-$C_4$ alkyl), phenyl($C_1$-$C_4$ alkoxy), phenylacetyl, $C_1$-$C_6$ alkanoyl, cyano, carbamyl, nitro, $C_1$-$C_6$ alkoxycarbonyl, methylenedioxy, $C_3$-$C_6$ alkylene, amino, —NH($C_1$-$C_4$ alkyl or benzyl), and N($C_1$-$C_4$ alkyl)$_2$;

$R_2$ is hydrogen, $C_1$-$C_6$ alkyl, carboxymethyl, $C_1$-$C_4$ alkoxycarbonylmethyl or a group of the formula

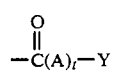

wherein t is 1 or 0; A is —$CH_2$—, —O—, —NH— or —N(-$C_1$-$C_6$ alkyl)—; and Y is phenyl or substituted phenyl as defined above;

$R_3$ is hydrogen or a group of the formula

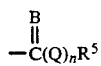

wherein B is O or S; n is 0 or 1; Q is —NH—, —N(-$C_1$-$C_6$ alkyl)—, —S—, or —O—; and $R^5$ is a group of the formula —[CH($R^6$)]$_q$—($CH_2$)$_r$—$R^7$ wherein $R^6$ is hydrogen or $C_1$-$C_6$ alkyl; q is 0 or 1; r is 0, 1 or 2; and $R^7$ is hydrogen, $C_1$-$C_8$ alkyl, $C_3$-$C_8$ cycloalkyl, pentafluorophenyl, pyridyl, tetrahydronaphthyl, indolyl, quinolinyl, phenyl, naphthyl, or phenyl or naphthyl substituted with 1, 2, or 3 substituents as defined above for phenyl; or the group —(Q)$_n$$R^5$ is 2-tetrahydroisoquinolinyl; and the pharmaceutically acceptable salts thereof; provided that at least one of the groups R or $R^1$ is other than hydrogen or $C_1$-$C_6$ alkyl, and R or $R^1$ is hydrogen only when the other of R and $R^1$ is substituted phenyl in which the substituent is phenyl; and provided further that at least one of the groups $R_2$ and $R_3$ is other than hydrogen, and when $R^3$ is a group of the formula

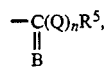

$R^2$ is other than a group of the formula

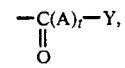

and a pharmaceutically acceptable carrier, excipient or diluent therefor.

2. A pharmaceutical formulation comprising as an active ingredient an effective amount of a compound of claim 1 where R3 is —C(B)(Q)$_n$—[CH($R^6$)]$_q$—($CH_2$-)$_r$—$R^7$, and a pharmaceutically acceptable carrier, excipient or diluent therefor.

3. A pharmaceutical formulation comprising as an active ingredient an effective amount of a compound of claim 1 where $R_3$ is —COH$R^7$ and a pharmaceutically acceptable carrier, excipient or diluent therefor.

4. A pharmaceutical formulation comprising as an active ingredient an effective amount of a compound of claim 3 wherein R,$R_1$ and $R^7$ are each phenyl or substituted phenyl and a pharmaceutically acceptable carrier, excipient or diluent therefor.

5. A method for inhibiting the interaction of cholecystokinin or gastrin with its receptors in a warm-blooded vertebrate thereby antagonizing the influence of endogenous cholecystokinin or gastrin which method comprising administering to said vertebrate a compound of A compound of the formula

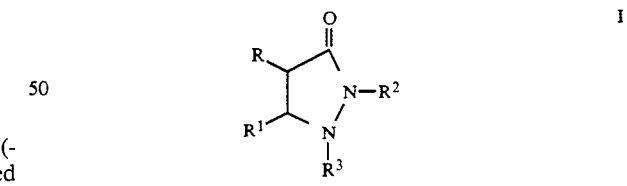      I wherein

R and $R^1$ are independently hydrogen, $C_1$-$C_6$ alkyl, phenyl, benzyl, naphthyl, pyridyl or substituted phenyl having 1, 2, or 3 substituents selected from the group consisting of $C_1$-$C_6$ alkyl, $C_1$-$C_6$ alkoxy, $C_1$-$C_6$ alkylthio, halo, trifluoromethyl, phenyl, phenoxy, phenyl($C_1$-$C_4$ alkyl), phenyl($C_1$-$C_4$ alkoxy), phenylacetyl, $C_1$-$C_6$ alkanoyl, cyano, carbamyl, nitro, $C_1$-$C_6$ alkoxycarbonyl, methylenedioxy, $C_3$-$C_6$ alkylene, amino, —NH($C_1$-$C_4$ alkyl or benzyl), and N($C_1$-$C_4$ alkyl)$_2$;

$R_2$ is hydrogen, $C_1$-$C_6$ alkyl, carboxymethyl, $C_1$-$C_4$ alkoxycarbonylmethyl or a group of the formula

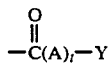

wherein
t is 1 or 0; A is —$CH_2$—, —O—, —NH— or —N(-$C_1$-$C_6$ alkyl)—; and Y is phenyl or substituted phenyl as defined above;
$R_3$ is hydrogen or a group of the formula

B is O or S n is 0 or 1; Q is —NH—, —N($C_1$-$C_6$ alkyl)—, —S—, or —O—; and $R^5$ is a group of the formula —[CH($R^6$)]$_q$—($CH_2$)$_r$—$R^7$ wherein $R^6$ is hydrogen or $C_1$-$C_6$ alkyl; q is 0 or 1; r is 0, 1 or 2; and $R^7$ is hydrogen, $C_1$-$C_8$ alkyl, $C_3$-$C_8$ cycloalkyl, pentafluoroophenyl, pyridyl, tetrahydro-naphthyl, indolyl, quinolinyl, phenyl, naphthyl, or phenyl or naphthyl substituted with 1, 2, or 3 substituents as defined above for phenyl; or the group —(Q)$_n$$R^5$ is 2-tetrahydroisoquinolinyl; and the pharmaceutically acceptable salts thereof;
provided that at least one of the groups R or $R^1$ is other than hydrogen or $C_1$-$C_6$ alkyl, and R or $R^1$ is hydrogen only when the other of R and $R^1$ is substituted phenyl in which the substituent is phenyl; and provided further that at least one of the groups $R_2$ and $R_3$ is other than hydrogen, and when $R^3$ is a group of the formula

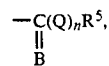

$R^2$ is other than a group of the formula

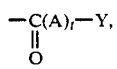

in an amount effective to antagonize the influence of cholecystokinin or gastrin in said vertebrate.

6. A method for treating irritable bowel syndrome which comprises administering to a warm blooded vertebrate an effective amount of a compound of the formula

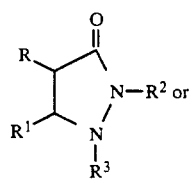

wherein
R and $R^1$ are independently hydrogen, $C_1$-$C_6$ alkyl, phenyl, benzyl, naphthyl, pyridyl or substituted phenyl having 1, 2, or 3 substituents selected from the group consisting of $C_1$-$C_6$ alkyl, $C_1$-$C_6$ alkoxy, $C_1$-$C_6$ alkylthio, halo, trifluoromethyl, phenyl, phenoxy, phenyl($C_1$-$C_4$ alkyl), phenyl($C_1$-$C_4$ alkoxy), phenylacetyl, $C_1$-$C_6$ alkanoyl, cyano, carbamyl, nitro, $C_1$-$C_6$ alkoxycarbonyl, methylenedioxy, $C_3$-$C_6$ alkylene, amino, —NH($C_1$-$C_4$ alkyl or benzyl), and N($C_1$-$C_4$ alkyl)$_2$;

$R_2$ is hydrogen, $C_1$-$C_6$ alkyl, carboxymethyl, $C_1$-$C_4$ alkoxycarbonylmethyl or a group of the formula

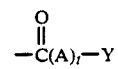

wherein
t is 1 or 0; A is —$CH_2$—, —O—, —NH— or —N(-$C_1$-$C_6$ alkyl)—; and Y is phenyl or substituted phenyl as defined above;
$R_3$ is hydrogen or a group of the formula

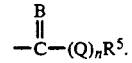

wherein
B is O or S
n is 0 or 1 Q is —NH—, —N($C_1$-$C_6$ alkyl)—, —S—, or —O—; and $R^5$ is a group of the formula —[CH($R^6$)]$_q$—($CH_2$)$_r$—$R^7$ wherein $R^6$ is hydrogen or $C_1$-$C_6$ alkyl; q is 0 or 1; r is 0, 1 or 2; and $R^7$ is hydrogen, $C_1$-$C_8$ alkyl, $C_3$-$C_8$ cycloalkyl, pentafluorophenyl, pyridyl, tetrahydro-naphthyl, indolyl, quinolinyl, phenyl, naphthyl, or phenyl or naphthyl substituted with 1, 2 or 3 substituents as defined above for phenyl; or the group —(Q)$_n$$R^5$ is 2-tetrahydroisoquinolinyl; and the pharmaceutically acceptable salts thereof;
provided that at least one of the groups R or $R^1$ is other than hydrogen or $C_1$-$C_6$ alkyl, and R or $R^1$ is other than hydrogen or $C_1$-$C_6$ alkyl, and R or $R^1$ is hydrogen only when the other of R and $R^1$ is substituted phenyl in which the substituent is phenyl; and provided further that at least one of the groups $R_2$ and $R_3$ is other than hydrogen, and when $R^3$ is a group of the formula

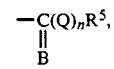

$R^2$ is other than a group of the formula

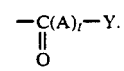

7. A method of claim 6 which comprises administering a compound of formula

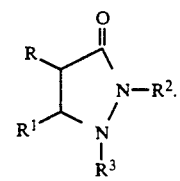

8. The method of claim 7 wherein $R^2$ is hydrogen.
9. The method of claim 8 wherein $R^3$ is a group —CB(Q)$_n$—[CH($R^6$)]$_q$—($CH_2$)$_r$—R7.
10. The method of claim 9 wherein q and r are 0.
11. The method of claim 10 wherein R, $R^1$ and $R^7$ are each phenyl or substituted phenyl.
12. The method of claim 11 wherein R and $R^1$ are in the trans stereochemical configuration.
13. The method of claim 9 wherein $R^7$ is bromophenyl.

* * * * *

UNITED STATES PATENT AND TRADEMARK OFFICE
CERTIFICATE OF CORRECTION

PATENT NO. : 5,300,514
DATED : April 5, 1994
INVENTOR(S) : Raymond F. Brown, et al.

It is certified that error appears in the above-indentified patent and that said Letters Patent is hereby corrected as shown below:

Column 50, line 27 reads "$-C(B)(Q)_n-$" should read "$-CB(Q)_n-$".

Column 50, line 45 reads "compound of A compound of the formula" should read "a compound of the formula".

Signed and Sealed this

Tenth Day of January, 1995

Attest:

BRUCE LEHMAN

Attesting Officer

Commissioner of Patents and Trademarks